(12) United States Patent
Hu et al.

(10) Patent No.: US 9,750,433 B2
(45) Date of Patent: Sep. 5, 2017

(54) USING HEALTH MONITOR DATA TO DETECT MACRO AND MICRO HABITS WITH A BEHAVIORAL MODEL

(71) Applicant: Lark Technologies, Inc., Mountain View, CA (US)

(72) Inventors: Julia Hu, Mountain View, CA (US); Jeff Zira, Mountain View, CA (US)

(73) Assignee: Lark Technologies, Inc., Mountain View, CA (US)

( * ) Notice: Subject to any disclaimer, the term of this patent is extended or adjusted under 35 U.S.C. 154(b) by 209 days.

(21) Appl. No.: 14/572,601

(22) Filed: Dec. 16, 2014

(65) Prior Publication Data

US 2016/0007912 A1    Jan. 14, 2016

Related U.S. Application Data

(60) Provisional application No. 61/916,708, filed on Dec. 16, 2013, provisional application No. 61/935,987, filed on Feb. 5, 2014.

(51) Int. Cl.
*A61B 5/11* (2006.01)
*A61B 5/00* (2006.01)

(52) U.S. Cl.
CPC ............ *A61B 5/1123* (2013.01); *A61B 5/002* (2013.01); *A61B 5/1118* (2013.01); *A61B 5/6824* (2013.01); *A61B 5/725* (2013.01); *A61B 5/7282* (2013.01); *A61B 5/1112* (2013.01); *A61B 5/6898* (2013.01); *A61B 2560/0242* (2013.01)

(58) Field of Classification Search
CPC .......................... A61B 5/1118; A61B 5/1123
See application file for complete search history.

(56) References Cited

U.S. PATENT DOCUMENTS

| | | | |
|---|---|---|---|
| 5,361,241 A | 11/1994 | Ferrara et al. | |
| 5,686,882 A | 11/1997 | Giani | |
| 5,764,594 A | 6/1998 | Berman et al. | |
| 5,966,346 A | 10/1999 | Arai | |
| 6,426,697 B1 | 7/2002 | Capowski et al. | |
| 6,527,711 B1 | 3/2003 | Stivoric et al. | |
| 6,595,929 B2 | 7/2003 | Stivoric et al. | |

(Continued)

FOREIGN PATENT DOCUMENTS

| | | | | |
|---|---|---|---|---|
| WO | 2012090226 A | 7/2012 | | |
| WO | WO 2013086363 A2 * | 6/2013 | ............. | A61B 5/002 |

*Primary Examiner* — Michael C Stout
*Assistant Examiner* — Nicholas E Kolderman
(74) *Attorney, Agent, or Firm* — Jeffrey Schox; Ivan Wong

(57) ABSTRACT

A method for communicating activity-related notifications to a user includes: receiving a record of activity events of a particular activity type performed by the user over a period of time; selecting a first time-based filter from a set of time-based filters; identifying a cluster of activity events in the record of activity events filtered according to the first time-based filter; identifying an early bound and a late bound on start times of activity events of the particular activity type from the cluster; communicating a notification of a first type to the user at a first time within a threshold time of the early bound on a day fulfilling the first time-based filter; and communicating a notification of a second type to the user at a second time within a threshold time of the late bound on a day fulfilling the first time-based filter.

20 Claims, 6 Drawing Sheets

(56) References Cited

U.S. PATENT DOCUMENTS

| | | |
|---|---|---|
| 6,605,038 B1 | 8/2003 | Teller et al. |
| 7,020,508 B2 | 3/2006 | Stivoric et al. |
| 7,050,360 B2 | 5/2006 | Saito |
| 7,153,262 B2 | 12/2006 | Stivoric et al. |
| 7,261,690 B2 | 8/2007 | Teller et al. |
| 7,285,090 B2 | 10/2007 | Stivoric et al. |
| 7,502,643 B2 | 3/2009 | Farringdon et al. |
| 7,689,437 B1 | 3/2010 | Teller et al. |
| 7,959,567 B2 | 6/2011 | Stivoric et al. |
| 7,974,849 B1 * | 7/2011 | Begole ............... G06Q 10/0631 705/1.1 |
| 8,073,707 B2 | 12/2011 | Teller et al. |
| 8,157,731 B2 | 4/2012 | Teller et al. |
| 2002/0170193 A1 | 11/2002 | Townsend et al. |
| 2004/0012502 A1 | 1/2004 | Rasmussen |
| 2004/0152957 A1 | 8/2004 | Stivoric et al. |
| 2005/0113650 A1 | 5/2005 | Pacione et al. |
| 2005/0131288 A1 | 6/2005 | Turner et al. |
| 2005/0190065 A1 | 9/2005 | Ronnholm |
| 2006/0136199 A1 | 6/2006 | Nongpiur et al. |
| 2006/0284979 A1 | 12/2006 | Clarkson |
| 2006/0293608 A1 | 12/2006 | Rothman et al. |
| 2008/0167535 A1 | 7/2008 | Stivoric et al. |
| 2009/0088220 A1 | 4/2009 | Persson |
| 2009/0147965 A1 | 6/2009 | Kuo |
| 2009/0203972 A1 | 8/2009 | Heneghan et al. |
| 2010/0057360 A1 | 3/2010 | Ohkubo |
| 2010/0099954 A1 | 4/2010 | Dickinson et al. |
| 2010/0113153 A1 | 5/2010 | Yen et al. |
| 2010/0195447 A1 | 8/2010 | George |
| 2010/0214216 A1 | 8/2010 | Nasiri et al. |
| 2011/0044501 A1 | 2/2011 | Tu et al. |
| 2011/0087076 A1 | 4/2011 | Brynelsen et al. |
| 2011/0112771 A1 | 5/2011 | French |
| 2011/0190593 A1 | 8/2011 | McNair |
| 2011/0196603 A1 | 8/2011 | Graham et al. |
| 2011/0254760 A1 | 10/2011 | Lloyd et al. |
| 2011/0320130 A1 | 12/2011 | Valdes et al. |
| 2012/0072168 A1 | 3/2012 | Yin et al. |
| 2012/0316686 A1 | 12/2012 | Dueckman |
| 2013/0216989 A1 | 8/2013 | Cuthbert |
| 2014/0335490 A1 | 11/2014 | Baarman et al. |
| 2015/0269850 A1 | 9/2015 | Rivera de la Vega et al. |

* cited by examiner

USING HEALTH MONITOR DATA TO DETECT MACRO AND MICRO HABITS WITH A BEHAVIORAL MODEL

CROSS-REFERENCE TO RELATED APPLICATIONS

This application claims the benefit of U.S. Provisional Application No. 61/916,708, filed on 16 Dec. 2013, and U.S. Provisional Application No. 61/935,987, filed on 5 Feb. 2014, both of which are incorporated in their entireties by this reference.

The application is related to U.S. Provisional Application No. 61/827,920, filed on 28 May 2013, U.S. Provisional Application No. 61/916,701, filed on 16 Dec. 2013, U.S. patent application Ser. No. 14/048,956, filed on 8 Oct. 2013, U.S. patent application Ser. No. 14/315,195, filed on 25 Jun. 2014, and U.S. patent application Ser. No. 14/315,195, filed on 25 Jun. 2014, which are incorporated in their entireties by this reference.

TECHNICAL FIELD

This invention relates generally to the field of digital health and more specifically to a new and useful method for communicating activity-related notifications in the field of digital health.

DESCRIPTION OF THE EMBODIMENTS

The following description of embodiments of the invention is not intended to limit the invention to these embodiments, but rather to enable any person skilled in the art to make and use this invention.

1. Method

Figure 1:
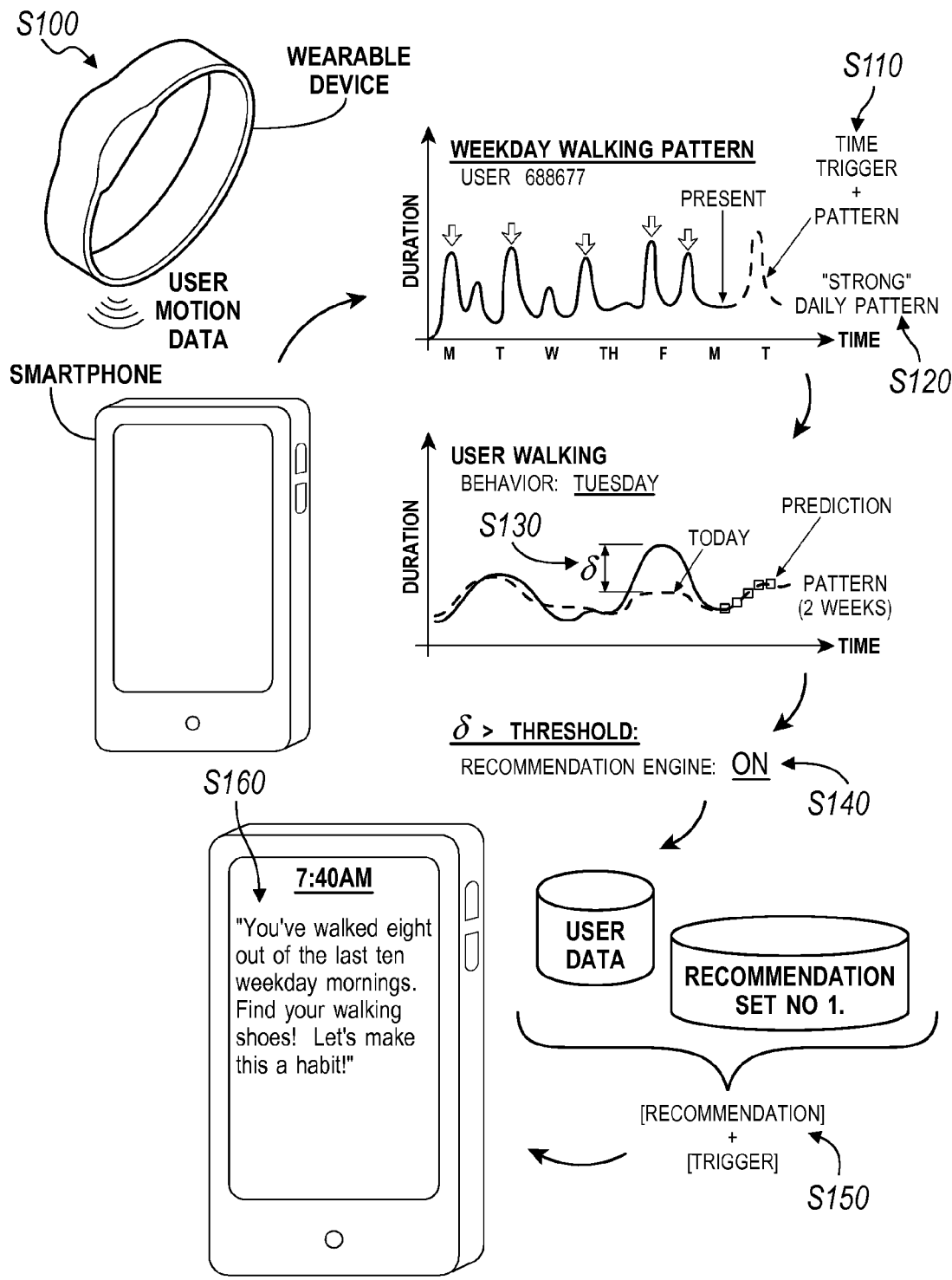
FIG. 1 is a flowchart representation of a method.

As shown in FIG. 1, a method for communicating activity-related notifications includes: detecting a pattern of a behavior by a user during a first time period in Block S110; classifying a strength of the behavioral pattern in Block S120; detecting a deviation from the behavior during a second time period of duration less than the first time period in Block S130; in response to a deviation from the behavior during the second time period, arming a recommendation for delivery to the user in Block S140; selecting the recommendation from a set of recommendations based on the strength of the behavioral pattern and a direction of the deviation from the behavior in Block S150; and presenting the recommendation to the user in response to a trigger corresponding to the behavioral pattern in Block S160.

Figure 4:
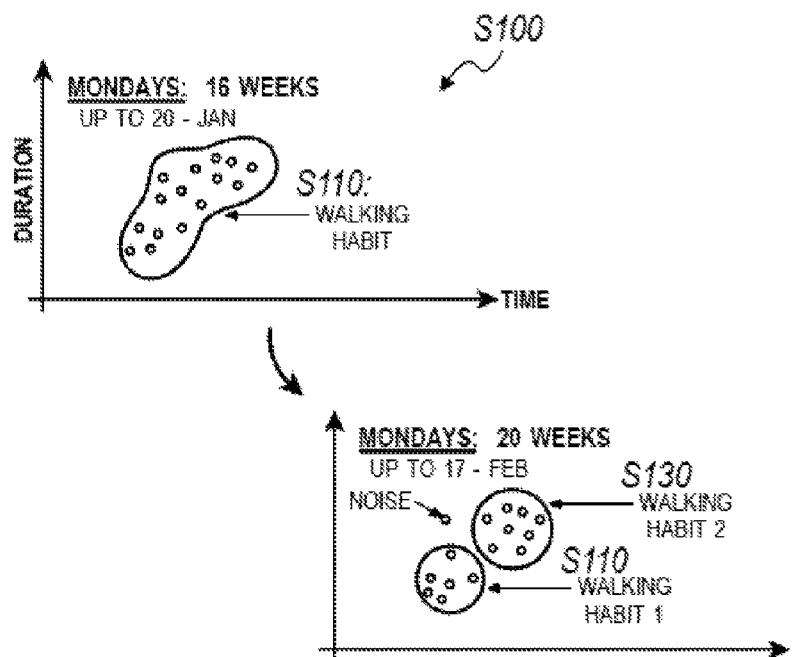
FIG. 4 is a flowchart representation of one variation of the method.
Figure 5A:
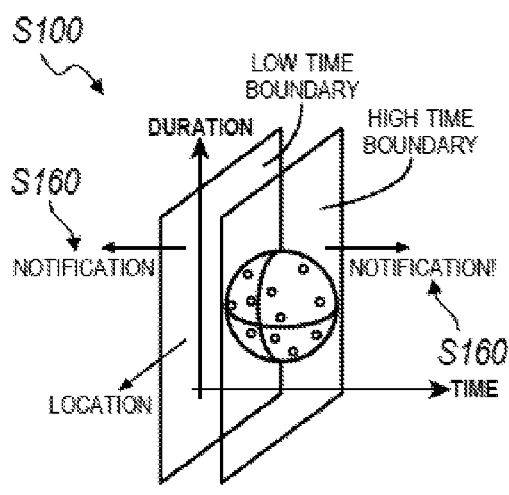
FIGS. 5A and 5B are flowchart representations of variations of the method.
Figure 5B:
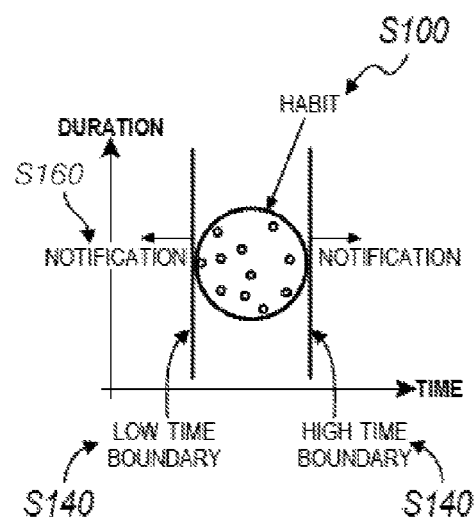

As shown in FIGS. 4, 5A, and 5B, one variation of the method for communicating activity-related notifications to a user includes: receiving a record of activity events of a particular activity type performed by the user over a period of time in Block S102, the record specifying a start time and a duration of each activity event in the record of activity events; selecting a first time-based filter from a set of time-based filters for the record in Block S110; identifying a cluster of activity events in the record of activity events filtered according to the first time-based filter in Block S110; identifying an early bound on start times of activity events of the particular activity type from the cluster of activity events in Block S140; identifying a late bound on start times of activity events of the particular activity type from the cluster of activity events in Block S140; at a first time succeeding the period of time, communicating a notification of a first type to the user in Block S160, the first time within a threshold time of the early bound on a day fulfilling the first time-based filter; and at a second time succeeding the period of time, communicating a notification of a second type to the user in Block S160, the second time within a threshold time of the late bound on a day fulfilling the first time-based filter.

Figure 6:
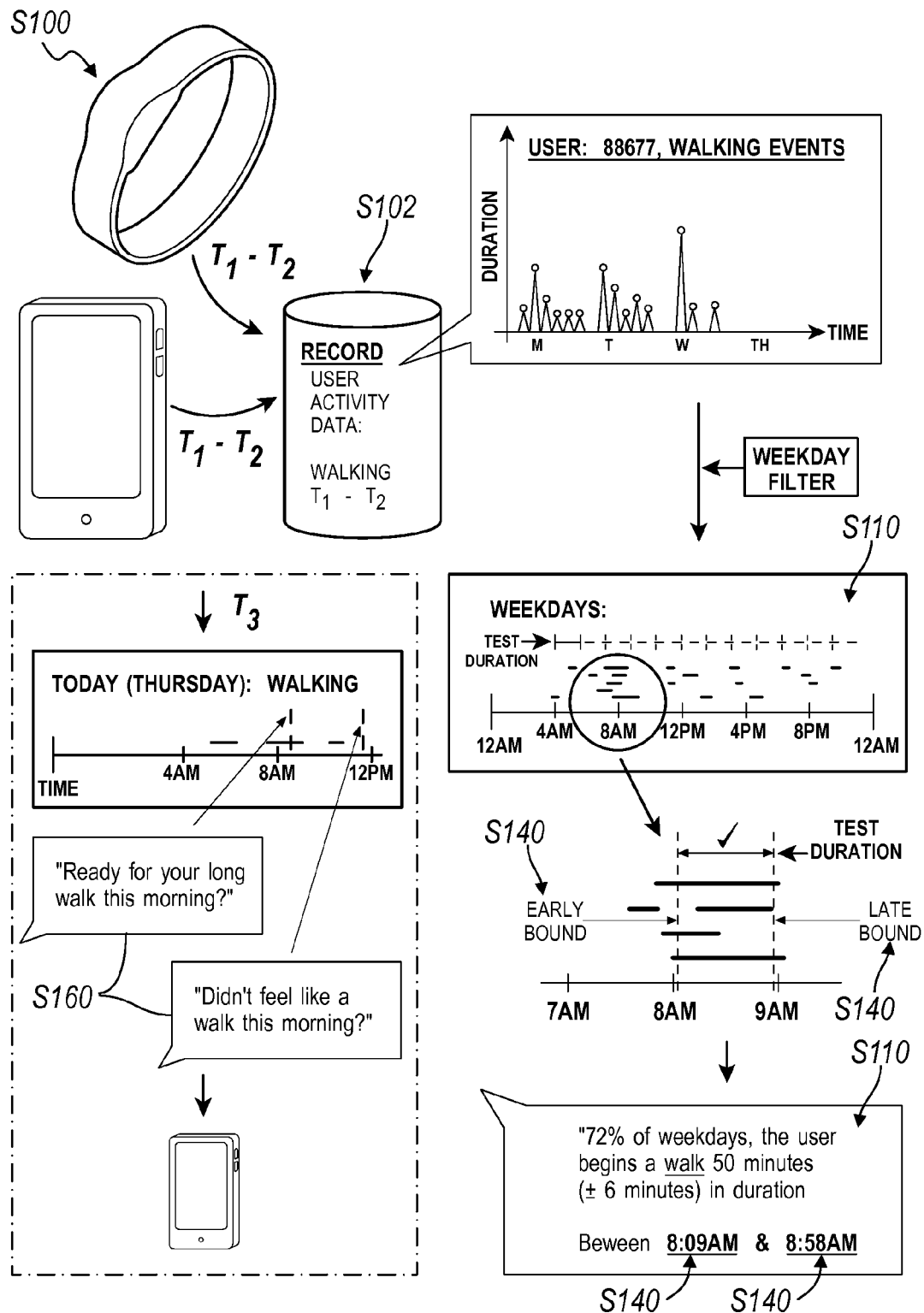
FIG. 6 is a flowchart representation of one variation of the method.

As shown in FIG. 6, a similar variation of the method includes: receiving a record of activity events of a particular activity type performed by the user over a period of time in Block S102, the record specifying a time of each activity event in the record of activity events; selecting a first time-based filter from a set of time-based filters for the record in Block S110; identifying a cluster of activity events in the record of activity events filtered according to the first time-based filter in Block S110; identifying an early bound on times of activity events of the particular activity type from the cluster of activity events in Block S140; identifying a late bound on times of activity events of the particular activity type from the cluster of activity events in Block S140; extrapolating, from the cluster, a quantitative datum corresponding to the particular activity type and the first time-based filter in Block S150; at a first time succeeding the period of time, presenting a form of the quantitative datum through a mobile computing device associated with the user in Block S160, the first time within a threshold time of the early bound on a day fulfilling the first time-based filter; and at a second time succeeding the period of time, in response to an absence of a detected activity of the particular activity type between the early bound and the late bound on a day fulfilling the first time-based filter, presenting to the user a prompt to provide feedback for the absence of a detected activity of the particular activity type in Block S160, the second time within a threshold time of the late bound on a day fulfilling the first time-based filter.

2. Applications

Generally, the method functions to detect a behavioral pattern of a user over a first period of time, to correlate the behavioral pattern of the user with a trigger, to identify a deviation from the behavioral pattern by the user within a second period of time succeeding (and/or shorter than) the first period of time, and to deliver a notification (e.g., a prompt, a recommendation) to based on the trigger in response to deviation from the behavioral pattern. The method can therefore be implemented within a habit-building program—such as within a wellness program executing on a wellness platform described in U.S. patent application Ser. No. 14/048,956—to select and deliver content to a user to support the user in building a positive behavioral pattern, sustaining a positive behavioral pattern (or "macro habit"), and/or weakening a negative behavioral pattern. In particular, the method can function to select a particular type of prompt to deliver to the user, to automatically construct the prompt, to determine when to deliver the prompt to the user based on an user behavioral pattern identified from user data collected over a period of time, based on a deviation from the behavioral pattern within a subsequent (e.g., short) period of time, and based on an identified trigger (e.g., time, location, weekday) corresponding to the behavioral pattern.

Figure 2:
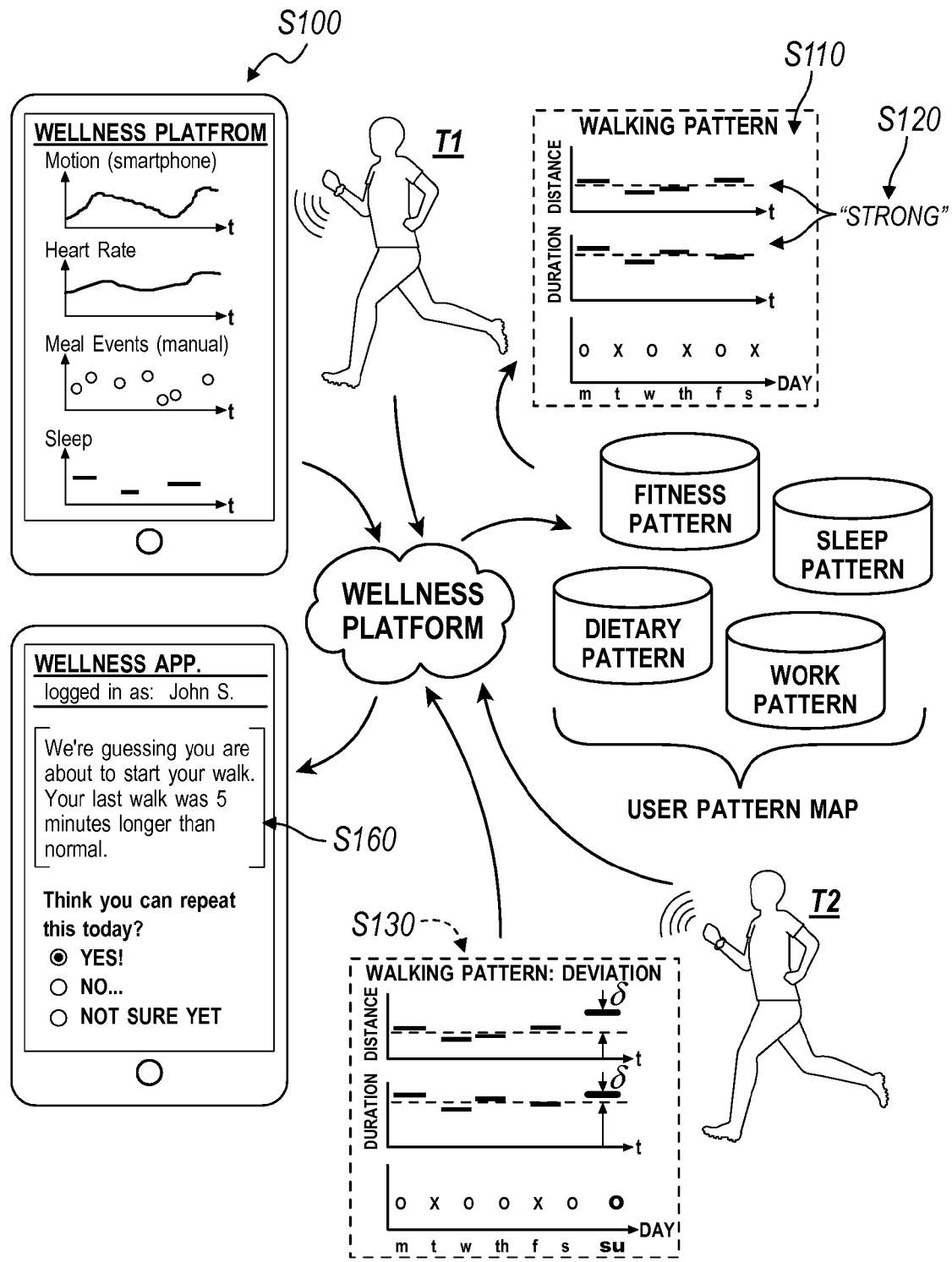
FIG. 2 is a flowchart representation of one variation of the method.

In one example, various Blocks of the method are implemented within a native wellness platform application executing on (or in conjunction with) a smartphone associated with a user, and the user interfaces with the smartphone to enter a goal of 'walking continuously over a period of ten minutes per day' into the native wellness platform application. In this example, Block S110 analyzes user motion data collected from the smartphone and/or from a wearable device worn by the user (e.g., a 'smart' wristband) over a two-week period (or "interval") to identify user walking patterns, such as based on or related to locations coincident a walking event, daily start times for walking events, durations of walking events, and/or other events or actions performed by the user before and/or after walking events, such as shown in FIGS. 1 and 2. In this example, Block S110 can implement a pattern engine to determine that, 'on average, the user completes one continuous nine-minute walk every weekday' or that, 'on average, the user completes one continuous nine-minute walk around every weekday starting within six minutes of 1:15 PM.' Block S130 can subsequently detect a deviation away from the detected behavioral pattern, such as to determine that 'the user did not complete a nine-minute walk today' or 'the user did not initiate a nine-minute walk between 1:09 PM and 1:21 PM today.' Based on such detected deviation from the detected behavioral pattern, Block S140 can arm a notification engine (e.g., a recommendation engine) to respond to the detected absence of the anticipated event, and Block S150 can implement the notification engine to select an appropriate prompt or other or directive for the user to guide the user back toward habitually fulfilling the (positive) behavioral pattern of walking after lunch. Block S160 can thus deliver the selected prompt to the user at a time substantially likely to elicit a response from the user.

In one implementation, Block S150 selects a prompt of a first type prompting the user to complete a walking event, and Block S160 delivers the prompt of the first type to the user immediately prior to anticipation of the user beginning a walking event on a subsequent weekday, such as at 1:08 PM on the subsequent weekday for the user who regularly walks around 1:15 (±6 minutes) each weekday. In another implementation, Block S150 selects a prompt of a second type asking the user to provide feedback for omitting the action from his daily routine, and Block S160 delivers the prompt of the second type to the user immediately upon determination that the user deviated from the predicted behavior, such as at 1:22 PM in the foregoing example.

The method can therefore populate messages relevant to a user and manage timely delivery of such messages to the user. The method can further support development and reinforcement of sub-habits (e.g., minor or "small" habits) to guide the user in developing larger, more involved habits out of multiple sub-habits over time. As in the foregoing example, the method can initially support the user in completing a ten-minute walk each weekday in order to guide the user in developing a more involved habit of completing multiple ten-minute walks each day or of completing one thirty-minute walk each weekday. However, the method can handle any other suitable behavioral pattern and/or habit, such as walking, running, eating well, sleeping, etc. and on any other timescale, such as hourly, daily, weekly, monthly, annually, etc., such as shown in FIG. 2.

As described in U.S. patent application Ser. No. 14/048,956, a native wellness platform executing on a mobile electronic device carried by the user (e.g., on a smartphone, tablet, smart watch, smart glasses, etc.) can implement the method to generate and deliver timely directives to the user. For example, Blocks of the method can be implemented within a native wellness platform application executing on a smartphone, the native wellness platform application supporting multiple internal wellness applications to guide and support the user in improving his wellness. Additionally or alternatively, one or more Blocks of the method can be implemented by an application server and/or within a user interface or user dashboard accessible through a web browser executing on a computer. Blocks of the method can also be implemented on one or more computer systems, such as a cloud-based computer system, a mainframe computer system, a grid-computer system, or any other suitable remote computer system. For example, the method can be implemented by a remote cloud-based computer system (e.g., a remote server) in communication with a smartphone carried by the user, wherein the remote computer system implements one or more Blocks of the method remotely to select or generate a prompt for the user, and wherein the remote computer system transmits the prompt back to the smartphone for presentation to the user. However, the method can be implemented by or in cooperation with any other one or more mobile computing devices, processors, computers, computer networks, etc.

Blocks of the method can therefore also interface with various hardware and/or software systems to collect user data and to present notifications to the user. For example, the method can interface with a "smart" wristband (or other wearable device) incorporating an accelerometer, a gyroscope, a temperature sensor, a magnetometer, and/or a display. For example, Block S110 can receive user motion, temperature, and/or other user-related data from the wearable device over time and extrapolate a user behavioral pattern and action triggers from these data. Blocks of the method can similarly interface with an external device—such as a bath scale or a digital environmental thermometer—to retrieve additional user or local environmental data. Blocks of the method can also interface with a mobile computing device (e.g., a smartphone) incorporating a GPS sensor, communication channels (e.g., email, SMS text messaging), and a display, etc. to retrieve relevant user data, location data, calendar data, communication data, etc. Block S160 of the method can further output notifications to the user through the mobile computing device, such as by displaying notifications on the display of the mobile computing device. One or more Blocks of the method can therefore aggregate various user and environment data from multiple sources and implement these data to generate and deliver notifications for the user.

3. Record of Activity Events

Block S102 of the method recites receiving a record of activity events of a particular activity type performed by the user over a period of time, the record specifying a start time and a duration of each activity event in the record of activity events. Generally, Block S102 functions to aggregate user and environmental data from multiple hardware devices, such as a wireless-enabled wearable wrist-borne device and a mobile computing device (e.g., smartphone) executing a native wellness platform, such as shown in FIG. 6.

In one implementation, Block S102 collects action data (e.g., a first set of action data) of the user from a wearable device worn by the user during the period of time, collects action data (e.g., a second set of action data) of the user from a mobile computing device associated with the user during the period of time, and fuses the action data from the wearable device and the mobile computing device into a register of discrete activity events performed by the user during the period of time. Block S102 can further filter the register of discrete activity events by activity type to assemble a record of activity events of a particular activity type; Block S102 can also apply multiple filters to the register of activity events to assemble multiple records, each containing documentation of activity events of a particular activity type. For example, Block S102 can generate a record of activity events containing documentation of walking, exercising, eating, driving, working, or sleeping events, the record further specifying a duration of each activity event in the record of activity events.

3.1 Wearable Device Data

Block S102 can interface with a wrist-borne device ("wristband") worn by the user both at night and during the day to collect user sleep- and activity-related data collected by the wristband. For example, the wireless-enabled wristband can incorporate an accelerometer, a gyroscope, a temperature sensor, and/or a display, such as a wearable device described in U.S. Provisional Application No. 61/710,867, filed on 8-Oct.-2012, which is incorporated in its entirety by this reference, and Block S102 can thus receive user motion, temperature, and/or other user-related data as the user wears the wristband during the day and/or at night. In one example implementation, Block S102 downloads raw acceleration data from the wristband. For example, Block S102 can execute on a smartphone carried by the user and store the raw acceleration data locally on the smartphone for manipulation in subsequent Blocks of the method. Block S102 can additionally or alternatively upload the raw acceleration data to a remote cloud-based computer system (e.g., a remote server) for analysis and extraction of relevant user action and user activity data from the raw acceleration data. These extracted data can then be communicated back to the smartphone for immediate implementation in subsequent Blocks of the method.

Yet alternatively, the wristband can process motion data locally, extrapolate specific user actions and/or activities from data collected locally, and output action and/or activity tags, such as described in U.S. patent application Ser. No. 14/315,195. In particular, the wearable device can locally compress raw motion data into one or more motion classifiers, such as compressed motion data (e.g., a compressed image of raw motion data), a user action (e.g., an instance extrapolated from compressed motion data), and a user activity (e.g., defined by a set of user actions). For example, the wearable device can generate action and/or activity tags (or timelines) and transmit these tags to the mobile computing device, and Block S102 can thus receive these tags substantially in real-time, such as substantially soon after generation on the wearable device, or asynchronously, such as every hour after a threshold number of user actions are identified, or every time a user activity (determined on the wearable device) changes with a suitable degree of confidence. However, Block S102 can collect user motion data from any other suitable type of wearable device worn in any other way by the user.

In one implementation, Block S102 collects user sleep data from the wristband while the user sleeps and/or after the user wakes from a period of sleep. For example, Block S102—executing on a smartphone—can sync (e.g., pair) with the wearable device (e.g., via Bluetooth), every morning once the user clears a silent alarm on the wearable device, the silent alarm indicating that the user is awake, that a period of user sleep has ended, and/or that the native wellness platform implementing the method should switch from a "user sleep" mode to a "user awake" mode. Block S102 can thus download user sleep data for the foregoing night and pass this data to subsequent Blocks of the method for analysis, such as to determine a quantity and a quality of the user's foregoing night of sleep. For example, the method can apply the user's sleep quality and/or quantity to predict a user energy level and/or energy level pattern throughout the forthcoming day, such as based on past user sleep and activity data. Subsequent Blocks of the method (e.g., Block S130) can also determine when the user went to bed (such as indicated by little to no movement after 9 pm), when the user woke (such as indicated by clearing an alarm through the wristband that also functions as a silent alarm), how long the user was in bed, how long it took the user to fall asleep, how many times the user woke during the night (such as indicated by certain movement patterns), the user's total time spent asleep, or the user's sleep quality (such as indicated by the total amount of user motion during sleep), etc. from sleep-related data collected from the wearable device in Block S102.

Block S102 can similarly receive user raw motion data or user activity and/or user action tags from the wearable device during the day, such as while the user eats, exercises, works, communes, etc. However, Block S102 can function in any other way to collect user action-related data over time from the wearable device, and subsequently Blocks of the method can analyze these data in any other suitable way.

3.2 Mobile Computing Device Data

Block S102 can similarly interface with a mobile computing device incorporating various sensors to collect relevant user data. For example, Block S102 can execute on a smartphone or tablet and collect raw sensor data from an accelerometer and/or a gyroscope incorporated within the mobile device. Like Block S102 and/or the wearable device described above, Block S102 can characterize local motion data from the mobile device into action or activity tags, timelines, etc. For example, Block S102 can identify a pattern in current acceleration data recorded through an onboard accelerometer and implement template matching to pair the behavioral pattern in the current acceleration data with a motion pattern of a known action, such as walking, running, biking, swinging (a tennis racket, a baseball bat), drinking, eating, watching television, sleeping, working at a computer, lifting weights, cooking, etc.

3.3 Additional Sensor Data

Block S102 can also interface with a sensor within the mobile computing device to determine a current location of the user. For example, Block S102 can interface with a Global Positioning System (GPS) sensor within the mobile computing device to retrieve a GPS coordinate position of the mobile computing device and then correlate this position with the current position of the user. Block S102 can additionally or alternatively interface with a cellular transceiver within the mobile computing device to triangulate the position of the mobile computing device relative to various local cellular towers. However, Block S102 can function in any other way to collect location data through the mobile computing device and to correlate these location data with the user's current (or previous) location.

Block S102 can similarly interface with other sensors within the mobile computing device to collect additional user and/or environmental data. For example, Block S102 can collect ambient light level data from a light sensor integrated into the mobile computing device, ambient noise level data from a microphone integrated into the mobile computing device, or ambient temperate data from a temperature sensor within the mobile computing device.

Block S102 can further interface with a local database on the mobile computing device or a remote databases in communication with the mobile computing device to collect additional user data. In various examples, Block S102 can interface with a local email client and/or an email server to collect user email information (e.g., email flux, timing, response types), a native phone call application or a voice-over-IP server to collect user phone call data, a device operating system or a media server to collect user media consumption data (e.g., music, video, images, consumption rate and trends), and/or a native calendar application or a personal data server to retrieve user calendar events and notes, etc. Block S102 can therefore interface with one or more data systems hosted internally on the mobile computing device or externally on a remote database, server, or computer system to access additional relevant user information.

Block S102 can similarly collect additional data from the wearable device, such as heart rate data collected through a heart rate sensor within the wearable device or user body temperate data collected through a temperature sensor within the wearable device. Block S102 can also interface with another standalone external device. For example, Block S102 can receive user weight data from a wireless-enabled digital bath scale or local ambient temperature or barometric pressure from a wireless-enabled thermometer or other environmental sensor. In these implementations, the mobile computing device hosting the native wellness platform can communicate with one or more external devices (e.g., the wearable device, a scale, an environmental sensor) over short-range communicate protocol, such as Bluetooth or Wi-Fi, or any other suitable communication protocol over any other suitable range.

3.1 Environmental Data

Block S102 can further function to retrieve environmental data from an external database and/or an external software system. For example, Block S102 can retrieve a local weather forecast for a location of the mobile computing device determined in Block S102, such as temperature, humidity, rainfall or chance of rain, and sunshine, fog, or cloud cover, etc.

3.5 Manual Data

Block S102 can also function to collect manual user entry of relevant user data, such as through a user interface within the native wellness platform executing on the mobile computing device.

In one implementation in which a wellness application within the native wellness platform is elected by the user, Block S102 selects a prompt defined by the wellness application, presents the prompt to the user, and collects the user's response to the prompt. In one example, a diet application—elected to the user's wellness account and executing within the native wellness platform on the user's mobile computing device—defines a prompt asking the user if and what he consumed for breakfast and a time window in which to present the prompt the user. In this example, Block S102 can select the prompt based on the time of day and communicate the prompt to the user, such as through a notification on the mobile computing device at the time specified by the diet application or based on a learned meal or dietary habit of the user (e.g., an average daily breakfast completion time for the user). In this example, once the user enters a response to the prompt, such as by selecting from a set of available responses or by inputting a custom textual response, Block S102 can pass the user's response to the corresponding diet application within the user's account. Block S102 can additionally or alternatively prompt the user to enter data through another device, such as by selecting an input region on a wearable device, by opening a web browser and completing a survey, etc. to collect a user response to a prompt defined within a wellness application.

In another implementation, Block S102 prompts the user to enter personal information. For example, Block S102 can present to the user a prompt reciting, "Hi Lily. What's the most important reason that you're dieting?" and subsequently collect a response from the user that includes, "I'm doing it for my kids." In this implementation, Block S102 can pass the user's response to Block S140 to select a subsequent directive for the user. As in the foregoing example, Block S140 can implement the user's response to generate a directive that includes, "Hi Lily. I know dieting is tough, but if you're having trouble, be sure to remember why you're doing it. You said that you were doing this for your kids." Block S102 can thus collect personal information from the user, and Block S140 can apply the user's personal information to generate custom, personal directives for the user.

Block S102 can also interface with the wearable device to collect user responses to an explicit or implicit prompt. For example, when the user consumes something, such as a glass of water, a snack, or a full meal, the user can record consumption by engaging an input region on the wearable device, such as by pressing and holding a button on the wearable device or double-tapping a surface of the wearable device. The wearable device can record the input as a consumption indicator and tag the input with a timestamp, such as according to an internal clock maintained by the wearable device. When the mobile computing device syncs with the wristband (e.g., every hour), Block S102 can download consumption indicators and associated time tags stored on the wearable device and add these consumption data to a timeline of user actions or activities. Block S102 can thus interface with the wearable device to log activity data, such as the time, type, size, etc. of a meal, by engaging a readily-accessible input region on a wearable device. Block S102 can further prompt and/or enable the user to add additional consumption details (e.g., a meal size, category, quality, content, etc.) to the consumption data received from the wearable device indicators, such as in real-time or asynchronously. By recording such additional user consumption data, Block S102 can enable subsequent Blocks of the method to further identify a relationship between user activity level, sleep patterns, etc. and user consumption.

3.6 Data Fusion

With any of the foregoing user data thus collected through one or more sensors integrated into one or more devices, Block S102 can extrapolate a user activity (or user action) from these data. Generally, Block S102 can implement machine learning, activity characterization algorithms, pattern extraction and recognition, statistical methods, template matching, lookup tables, or any other suitable analytic technique to determine a user action or activity from raw or compressed motion data thus collected. For example, Block S102 can implement pattern recognition to analyze accelerometer and/or gyroscope data collected from over a period of time from the wearable device and the mobile computing device associated with the user and to automatically group identified user actions (or activities) based on classifications of recognized motion patterns. In this example, Block S102 can analyze raw three-dimensional accelerometer data to count the user's steps. Block S102 can similarly classify motion data as any of biking, walking, driving, raking the grass, playing tennis or basketball, swimming (and the user's type of stroke), etc. Block S102 can also determine if the user is sedentary, such as based on a period of composite accelerometer (e.g., three-axis) amplitudes falling below a threshold acceleration. Block S102 can also characterize user motion data to determine if the user is sleeping and/or the user's current sleep cycle. For example, for acceleration data recorded through the wristband worn on the user's wrist, Block S102 can correlate small, high amplitude, oscillatory accelerations accompanied by little or no gradual, low amplitude acceleration with typing and little to no overall acceleration with sleeping or resting. Block S102 also can correlate smaller amplitude, more gradual, and oscillatory accelerations with walking and similar, higher-amplitude accelerations with jogging or running, through Block S102 can correlate raw user motion data with any other action or activity.

Block S102 can therefore identify a user activity (or action, combination of actions) from motion data collected through the mobile computing device, the wearable device, etc. substantially in real-time, such as within one minute of user initiation of an action or activity. Block S102 can alternatively correlate motion data from a user activity asynchronously, such as by analyzing motion data within predefined time periods or blocks (e.g., in thirty-minute time blocks).

3.7 Record

As activity events are thus identified over time, Block S102 can aggregate these activity data in a record of activity events based on activity type. Block S102 can also incorporate additional data—such as start time, duration, location, intensity, distance (e.g., for running or walking activities), quality (e.g., for sleep periods), etc. —for one or more activity events noted in the record. In one example, Block S102 generates a record of walking events performed by the user over a sequence of days, the record specifying a start time and a duration of each walking event in the record of walking events. In this example, the method can then select a time-based filter specifying a minimum duration of a walking event and a particular subset of weekdays on which such walking events are performed by the user, and the method can subsequently discard walking events—in the record of walking events—of duration less than the minimum duration and occurring on days outside the particular subset of weekdays to identify a cluster of activity events—in the record of activity—indicative of a behavioral pattern, as described below.

Alternatively, Block S102 can retrieve such a record of activity events previously assembled, such as a record generated by a remote application server executing methods and techniques similar to those described above.

4. Behavioral Pattern Detection

Block S110 of the method recites detecting a behavioral pattern of a user from a record of activity events—of a particular activity type—performed by the user during a first time period. Generally, Block S110 implements a pattern engine to extrapolate a behavioral pattern (e.g., a "macro habit") from user motion, location, and/or related event data collected over a relatively long period of time (e.g., one or two weeks) from a wearable device worn by the user and/or from a mobile computing device carried by the user. Block S110 can extrapolate from these data a behavioral pattern pertaining to a particular type of behavior elected by the user for adoption or reinforcement. For example, Block S110 can match a behavioral pattern extrapolated from these user data with a walking-, exercising-, sleeping-, or working-related behavior elected for adoption by the user. Block S110 can also identify various behavioral patterns of the same, similar, or dissimilar types, such as three most-likely or most-valuable user behavioral patterns, as described below, and then pass any one or more of these three behavioral patterns to subsequent Blocks of the method to trigger recommendations for building and/or maintaining related habits.

In one implementation, Block S110 assembles action and/or activity data collected through the user's mobile computing device and/or wearable device—as described in U.S. patent application Ser. No. 14/315,195—into a timeline of user behaviors. Block S110 then compares similar actions across the timeline according to various timescales and with varying tolerances to identify repeated user actions or activities indicative of a behavioral pattern. In one example, as shown in FIG. 1, Block S110 can identify walking events completed by the user during a running period of two-weeks timeline and group the walking events by start times and durations, such as according to preset or user-specific start time ranges and duration ranges. In this example, Block S110 can compare start times of walking periods of similar duration occurring every day within the two-week period, occurring every weekday during the two-week period, occurring every Sunday, Monday, and Thursday during the two-week period, occurring every Friday during the two-week period, occurring every four-hour period of daylight on weekends during the two-week period, occurring every hour of daylight during the weekdays of the two weeks period, and/or occurring on any other time basis.

Block S110 can thus identify—from user data collected over a period of time—a set of possible behavioral patterns, each possible behavioral pattern defining a type of activity (e.g., walking) with a range of start times within a corresponding timescale. For example, Block S110 can extrapolate a first potential behavioral pattern indicating that the user "walks 3±1 minutes starting between 8:30 AM and 10:15 AM on Mondays and Tuesdays," a second potential behavioral pattern indicating that the user "walks 8±3 minutes starting between 12 PM and 1 PM on Wednesdays," and a third potential behavioral pattern indicating that the user "walks 22±3 minutes starting between 7:30 AM and 7:45 AM on weekdays."

In this implementation, Block S110 can then calculate a probability that the user would substantially randomly perform a similar activity within a corresponding indicated range of start times and of corresponding durations on a date fulfilling the corresponding time basis. In particular, Block S110 can estimate a higher probability of random repetition of an activity by the user for a possible behavioral pattern characterized by larger variations in duration and/or start times of the activity on days (or within other periods) fulfilling the selected time basis (and vice versa), and the method can thus correlate a lower probability—calculated in Block S110—with a stronger likelihood that the repeated action corresponds to a behavioral pattern. For example, Block S110 can assign a first potential behavioral pattern (indicating that the user "walks 3±1 minutes starting between 8:30 AM and 10:15 AM on Mondays and Tuesdays") with a highest probability of including substantially random walking events and therefore a lowest likelihood of being a pattern, can assign a second potential behavioral pattern (indicating that the user "walks 8±3 minutes starting between 12 PM and 1 PM on Wednesdays") with a moderate probability of including substantially random walking events and therefore a moderate likelihood of being a pattern, and can assign the third potential behavioral pattern (indicating that the user "walks 22±3 minutes starting between 7:30 AM and 7:45 AM on weekdays") with a lowest probability of including substantially random events and therefore a highest likelihood of being a pattern. Block S110 can then prioritize and/or filter possible behavioral patterns according to corresponding probabilities that repetitions of activity associated therewith—on the selected time basis—are substantially random. For example, Block S110 can select a particular behavioral pattern—from a set of identified possible behavioral patterns potentially related to a current habit program engaged by the user—corresponding to a lowest probably of containing records of random activity events. Subsequent Blocks of the method can thus identify deviation from this particular behavioral pattern and deliver notifications related to the particular behavioral pattern to the user.

Block S110 can further assign a time-based trigger to a selected (e.g., identified) behavioral pattern. In particular, Block S110 can correlate a time-related variable with a trigger for user performance of the activity of the behavioral pattern. For example, for the third potential behavioral pattern described above, Block S110 can identify "7:30 AM and 7:45 AM on weekdays" as a time-based trigger for "walking 22±3 minutes" on a weekday (e.g., Monday through Friday) time basis. Thus, in this example, Block S110 can group repeated walking activities starting approximately between 7:30 AM and 7:45 AM on weekdays and of durations approximately between 19 and 25 minutes into a behavioral pattern, set 7:30 AM as an early bound on beginning a walking event on a weekday, and set 7:45 AM as a late bound on beginning a walking event on a weekday; subsequent Blocks of the method can thus deliver a walking-related prompt of a first type to the user in response to approach of the 7:30 AM early bound on a weekday, and subsequent Blocks of the method can similarly deliver a walking-related prompt of a second type to the user in response to passage of the 7:45 AM late bound on a weekday and a detected absence of the expected walking event.

Block S110 can further combine location, calendar, and/or other related event data collected through the user's mobile computing device and/or wearable device with a record or activity events collected over a period of time to form a (virtual) map of user behaviors over time and/or over various locations and then filter these activity events according one or more selected time bases (e.g., weekdays, weekends, Mondays and Tuesdays, or the first week of every month). Block S110 can then identify groups of activity events of similar types, occurring in the same or similar locations (e.g., with a threshold ground distance), occurring within a threshold period of time after the user's presence in the same or similar location, occurring (e.g., starting, ending) within a (static or dynamic) threshold time, and or corresponding to the same or similar durations within a (static or threshold) time range. Block S110 can thus correlate each groups or "clusters" containing more than a minimum or threshold of number activity events with a behavioral pattern. Block S110 can also set or adjust location tolerances, start times tolerances, duration tolerances, etc. to achieve a target number of activity events in a group and then implement methods or techniques described above to calculate a probably that future repetition of the activity type of the group by the user and fulfilling parameters of the group may be substantially random.

Block S110 can also manipulate location tolerances, start times tolerances, duration tolerances, weather-related parameters, leading event detection, etc. to set location, weather, calendar, and/or other related triggers for delivery prompts related to the behavioral pattern to the user. For example, Block S110 can determine that the user walks 9±3 minutes between 2 PM and 2:15 PM on weekdays on which the user enters his workspace by 10 AM but does not complete this walking event on weekdays on which he arrives at work after 10 AM, and Block S110 can thus tag this walking-based behavioral pattern with a location and an event (e.g., arrival at a particular location on or before a particular time) that must be satisfied to trigger delivery of a related notification to the user. In another example, Block S110 can determine that the user walks 15±4 minutes when the user nears a particular location, such as a grocery store, and Block S110 can thus tag this behavioral pattern with a particular location and a threshold range from the particular location that must be occupied by the user (e.g., the user's mobile computing device) in order to trigger delivery of a related notification to the user.

However, Block S110 can function in any other way to extrapolate a user behavioral pattern from user data over any other suitable period of time and to associate an identified behavioral pattern with any other suitable type of trigger. As described above, Block S110 can elect a single behavioral pattern as exhibiting a greatest correlation with and/or probability of being an established user habit, and Block S110 can thus pass this pattern to subsequent Blocks of the method. Block S110 can also elect and pass any other number and type of behavioral patterns to subsequent Blocks of the method. Block S110 can additionally or alternatively cooperate with Block S130 to implement machine learning to determine whether a series of user actions indicate a pattern and to then apply classifiers of the behavioral pattern to individual user actions to determine if a singular event qualifies as a deviation from that pattern.

5. Filters

Block S110 can therefore also function to select a time-based filter—from a set of time-based filters—for application to the record of activity events to enable detection of one or more behavioral patterns from the record. In particular, for a record containing documentation of activity events of a particular activity type, days (e.g., dates) on which the user performed the activity events, and start times and durations of the activity events, Block S110 can select a time-based filter defining a cycle time and/or a cycle trigger for repetition of the activity type by the user. Block S110 can then test the selected time-based filter to group arrange documentation of activity events occurring serially over time into a spatial distribution of activity events. As described above, Block S110 can then identify activity events in the spatial distribution of activity events as either an outlier or belonging to a cluster of like activity events and correlate a cluster of activity events with a (possible) behavioral pattern (e.g., habit), such as if a number of activity events contained within a cluster exceeds a threshold number.

In one example, Block S110 selects a filter specifying a test for a weekly cycle of repetition of the activity type, and Block S110 populates the filter with cycle triggers corresponding to days of the week on which repetition of the activity type may indicate a behavioral pattern. In this example, Block S110 can select a first filter specifying a weekly cycle and repetition of the activity type on all weekdays within a week, and Block S110 can aggregate all activity events, in the record, occurring on weekdays (within the first period of time) into a spatial distribution based on a time of the day that each activity event was initiated and the duration of each activity event based on the filter. In this example, if the first filter fails to yield a cluster of activity events of sufficient number or density, Block S110 can select a second filter to test on the record of activity events, such as a second filter specifying a test for a weekly cycle of repetition of the activity type and populated with cycle triggers corresponding to Mondays, Tuesdays, and Thursdays on which repetition of the activity type may indicate a behavioral pattern. Block S110 can thus apply the second filter to the record of activity events to generate a spatial distribution of a subset of activity events performed by the user on Mondays, Tuesdays, and Thursdays—according to the second filter—based on a time of the day that each activity event was initiated and the duration of each activity event. Block S110 can continue to test alternative filters on the record of activity events until one (or a minimum number of) cluster of activity events of sufficient number or density to indicate a behavioral pattern is identified. For example, Block S110 can sequentially test the record of activity events against a filter specifying a single weekday, a filter specifying a combination of two weekdays, a filter specifying a combination of three weekdays, a filter specifying a combination of four weekdays, a filter specifying a combination of five weekdays, a filter specifying a single weekend day, and a filter specifying a combination of weekend days, etc. and/or select a particular filter from a set of filters containing the foregoing filters.

Block S110 can additionally or alternatively select filters specifying bi-weekly, monthly, quarterly, semi-annually, annually, or any other cycle duration or combination of cycle durations, such as based on a period of time over which activity events in the record were collected. For example, Block S110 can select a bi-weekly cycle specifying repetition of an activity type on the first Monday and Wednesday of the bi-weekly cycle. In another example, Block S110 can select a monthly cycle specifying repetition of an activity type on the first Friday of the monthly cycle. In yet another example, Block S110 can select an annual cycle specifying repetition of an activity type on weekends of the month of June in the annual cycle.

Block S110 can similarly select a filter (or populate a time-based filter with a parameter) specifying one or more of a minimum duration of an activity event, a maximum duration of an activity event, a location or range of locations coincident an activity event, an intensity of an activity event, distance traversed during an activity event, quality an activity event, etc. Block S110 can thus apply such a filter to the record of activity events to filter the activity events in the record by an additional dimension (e.g., duration, location, intensity, quality, etc.). Block S110 can further aggregate activity events into a spatial distribution representative of the multiple dimensions of the activity events and identify (presence of absence of) clusters in the spatial distribution, as described above.

6. Behavioral Pattern Strength

One variation of the method includes Block S120, which recites classifying a strength of the behavioral pattern. Generally, Block S120 functions to estimate a confidence in subsequent repetition of the action or activity by the user in response to one or more triggers and to classify the behavioral pattern on a short time scale (i.e., shorter than the first period) accordingly, as shown in FIG. 1. In one implementation, Block S120 classifies the behavioral pattern identified in Block S110 as one of a strong pattern (CASE 1), a medium or growing pattern (CASE 2), and a weak pattern (CASE 3) based on a range of start times and/or a durations, etc. of an action or activity specific to the behavioral pattern. For example, Block S110 can identify a behavioral pattern specifying that the user completes one continuous ten-minute walk every weekday but at widely varying times ranging between 7 AM and 9 PM, and Block S120 can classify this pattern as weak (CASE 3). In this example, though Block S110 determines that the user is substantially likely to walk everyday, and Block S120 can classify this pattern as weak because the user has not yet developed a consistent (micro) habit around walking at a particular time, thus indicating a low confidence in the accuracy of a predicted start time and duration of a subsequent walk. (In particular, a (micro) habit can be defined as an action that the user consistently perform within a set time window, when near a particular location, and/or in response to a particular event.) In another example, Block S110 can identify a behavioral pattern specifying that the user completes one continuous 12±3 minute walk every weekday and beginning between 7 AM and 8 AM, and Block S120 can classify this pattern as moderate (CASE 2). In this example, Block S110 determines that the user is substantially likely to walk everyday at a time that is roughly consistent, and Block S120 can classify this pattern as moderate, thus indicating a moderate degree of confidence in the accuracy of a predicted start time and duration of a subsequent walk. In yet another example, Block S110 can identify a behavioral pattern specifying that the user completes one continuous 11±2 minute walk every weekday and beginning between 7 AM and 7:10 AM, and Block S120 can classify this pattern as strong (CASE 1). In this example, Block S120 can classify this pattern as strong due to the consistency with which the user begins and ends the walk on a regular schedule, thus indicating a high confidence in the accuracy of a predicted start time and duration of a subsequent walk.

In particular, Block S120 functions to calculate a predicted accuracy of a user action or activity specific to the behavioral pattern in response to a corresponding trigger, such as a time of day, occurrence of an event, or proximity to a location, and to classify the strength of the behavioral pattern based on the predicted accuracy of the corresponding action or activity. However, Block S120 can function in any other way to assign any other classification to the behavioral pattern output in Block S110.

7. Deviation

Block S130 of the method recites detecting a deviation from the behavior during a second time period of duration less than the first time period. Generally, Block S130 functions to implement a pattern finder to determine if the user completed an action or activity specified in the behavioral pattern in response to a recent trigger and to characterize an extent of deviation from the behavioral pattern if the user completed the action or activity. For example, Block S130 can implement methods and techniques described in U.S. patent application Ser. No. 14/048,956 to detect a deviation from the detected user behavioral pattern.

In one implementation, Block S130 determines if the user has completed an activity (or action) specified in the behavioral pattern (such as within a tolerance of duration, intensity, etc.) or has deviated from the specified activity in some way in response to detection of related trigger, such as passage of a window of time in which the user was predicted or expected to repeat the activity. In one example, Block S110 extrapolates a walking-related behavioral pattern from fourteen consecutive days of user walking data. In this example, if a walking event is anticipated on a present day based on the detected behavioral pattern, and if the user performs a walking event of duration within a threshold range (e.g., two minutes) of a duration characteristic of the walking-related behavioral pattern at least once on and by the end of the present day, Block S130 can thus determine that the user has not deviated from the behavioral pattern, and Block S140 can thus withhold presentation of a prompt to perform a walking event to the user, as in subsequent Blocks of the method (i.e., because the user already completed the activity as expected and does not need additional reminding). However, in this example, if the user does not walk at all or performs a walking event of duration substantially less e.g., at least 20% less) than the duration characteristic of the detected behavioral pattern on the present day despite a detection of a trigger indicative of performance of the activity by the user, Block S130 can determine that the user has deviated from the behavioral pattern, and subsequent Blocks of the method can deliver a directive or other prompt related to the behavioral pattern to the user (i.e., because the user may need support and/or guidance to establish and/or maintain the behavioral pattern of behavior). Furthermore, in this example, if the user performs a walking event of duration substantially greater (e.g., at least 20% greater) than the duration characteristic of the behavioral pattern more than the duration specified in the behavioral pattern) on the present day, Block S130 can determine that the user is forming a habit related to the behavioral pattern, and subsequent Blocks of the method can deliver related prompts to the user, such as recognition of the user's efforts in order to reinforce the user's positive behaviors.

Block S130 can thus test for completion of and/or deviation from a pattern in response to a detection or passage of a trigger (e.g., a time window, an event, proximity to a location, etc.) associated with the behavioral pattern. For example, Block S130 can test for deviation from the habit at midnight everyday or at the end of a time window characteristic of initiation of the activity type by the user, as identified in Block S110. Furthermore, if the user performs the activity approximately as anticipated according to the behavioral pattern, subsequent Blocks of the method can withhold prompts to perform the activity or otherwise deliver prompts to the user to commend the user's positive actions. Similarly, if the user does not perform the activity type as anticipated according to the behavioral pattern, subsequent Blocks of the method can implement a recommendation engine to deliver a directive or other message to the user to provide additional, reactive guidance to the user and/or to collect feedback from the user for reasons that the user did not perform the activity. However, Block S130 can function in any other way to identity deviation from the behavior.

Block S140 of the method recites, in response to a deviation from the behavior during the second time period, arming a recommendation for delivery to the user the user. Generally, Block S140 functions to selectively enable Blocks S150 and S160 in preparation for performance of the activity type by the user and/or based on the user's deviation from the behavioral pattern.

8. Notifications

Block S150 of the method recites selecting the recommendation from a set of recommendations based on the strength of the behavioral pattern and a direction of deviation from the behavior. Generally, Block S150 functions to select directives, recommendations, and/or directives to support the user in returning to the (positive) pattern if the user deviated away from the behavioral pattern and to reward or congratulate the user in building a stronger (positive) pattern (shown in FIG. 2). Block S150 can also account for the strength of the behavioral pattern (as determined in Block S110) to select a directive for the user. Block S150 can also set a delivery time for the directive based on a trigger corresponding to the behavioral pattern (as identified in Block S110) and the strength of the behavioral pattern.

In particular, Block S150 can function to select a directive that is particularly relevant to the user's behavior(s) and to set a time, location, event, and/or other trigger for delivery of the directive to the user such that the user is presented with the related information (e.g., through the wellness platform) substantially only at an instances in time in which the user is substantially likely to positively respond to the directive. For example, if Block S130 determines that the user has not deviated substantially from a behavioral pattern, Block S150 may refrain from selecting a directive for the user as the user is acting as expected according to identified behavioral patterns. However, if, at 11:59 PM on a present day, Block S130 determines that the user did not complete a walking event as specified in a behavioral pattern, Block S150 selects a directive to prompt the user to perform a walking event but delays delivery of the directive until a time at which the user is substantially likely to respond to the directive by beginning a walk (e.g., just before a next anticipated walking event). In particular, in this example, unless the behavioral pattern indicates that the user commonly walks at 11:59 PM, Block S150 can withhold delivery of the directive to the user as 11:59 PM since the user is unlikely to get out of bed and go for a walk. Rather, if the behavioral pattern indicates that the user commonly begins a walk between 7:30 AM and 7:45 AM on weekdays, Block S150 can set 7:39 AM on the next weekday as a delivery time for the directive, and Block S160 can present the directive on the users smartphone (or wearable device, or other computing device) at 7:39 AM on the next weekday on which the user is expected to perform such as walking event. Thus, for strong behavioral patterns (e.g., a CASE 1 pattern and some CASE 2 patterns) identified in Block S120, Block S150 can define a particular time, event, location, and/or other trigger for delivery of the directive to the user in Block S160.

Similarly, if Block S120 classifies the behavioral pattern as low strength (i.e., low trigger consistency, CASE 3), Block S150 can set a scattershot delivery schedule for the directive (or similar reminders, notifications, messages, etc.) over the next day during which the user is expected to perform the activity, as indicated by the detected behavioral pattern. Block S160 can thus deliver one or more directives to the user over a subsequent time period (e.g., between 8 AM and 8 PM on the following day), such as every hour, every time the user has walked continuously for more than one minute, or whenever another user with a similar behavioral pattern is within a threshold range of the user, etc. However, Block S150 can function in any other way to set time, event, location, and/or other triggers for delivery of a directive to the user for execution in Block S160.

As described above, Block S150 can select the directive from a pre-populated set of directives. In one implementation, Block S150 selects a generic directive from a set of directives and customizes the directive with recently-collected user data, such as described in U.S. Provisional Application No. 61/827,920. For example, if the user did not complete a ten-minute walk on the present weekday contrary to the behavioral pattern indicating that the user walks at a regular time on weekdays (e.g., CASE 1), Block S150 can select a directive reciting, "You've walked eight out of the last ten weekdays between 7:30 and 8 AM. It's 7:28, so find those walking shoes and hit the trail!," and Block S160 can present the directive to the user at 7:28 the next weekday morning. In another example, if the user did not complete a ten-minute walk on the present day contrary to the behavioral pattern indicating that the user walks, though not at a regular time (e.g., CASE 3), Block S150 can select a first directive reciting, "A ten-minute walk will give you an energy boost equivalent to one cup or coffee. It's 7 AM—why not skip the coffee maker and grab your walking shoes?" and select a second directive reciting, "Feeling sluggish? It's 2 PM—how about a quick walk around the block for some fresh air?," and Block S160 can present these directives to the user sequentially throughout the next weekday.

Thus, Block S150 can select, customize, and/or generate different reminders, directives, and/or prompts for the user based on different strengths of the behavioral pattern and how the user has deviated from the behavioral pattern. For example, Block S150 can select the directive from a first set of directives for the behavioral pattern that is classified as strong and from a second set of directives for the behavioral pattern that is classified as weak. However, Block S150 can function in any other way to generate feedback and to set a time or other trigger for delivery of the feedback to the user.

Block S160 of the method recites presenting the recommendation to the user in response to detecting of a trigger event associated with the behavioral pattern. Generally, Block S160 functions to deliver the directive (selected or generated in Block S150) to the user at an instance in which the directive is substantially actionable for the user (e.g., at an instance in which the user is substantially likely to perform or to prepare to perform an action noted in the directive). For example, Block S160 can present the directive at a substantially low-risk instance, such as in response to detected occurrence of a trigger associated with a strong behavioral pattern. In particular, Block S160 can monitor time (e.g., an international clock), user motion data, user location, local environmental, and/or other data collected through the user's wearable device, the user's mobile computing device, a remote computer network (e.g., a weather server), etc. to test for or predict upcoming occurrence of a trigger related to the directive.

Once a time, location, event, or other trigger is detected or is predicted with a suitable degree of confidence, Block S160 can present the directive to the user. For example, as described in U.S. Provisional Application No. 61/827,920, Block S160 can render the directive in text format on a display of the user's mobile computing device, such as in the form of a notification within a native wellness platform application executing on the user's smartphone, on a locked screen of the device, or on a home screen of the device. Alternatively, Block S160 can display the directive on the user's wearable device or deliver the directive audibly through an intelligent personal assistant executing on the user's mobile computing device and/or on the user's wearable device.

In one implementation, Block S160 delivers the directive within a textual conversation presented to the user within a messaging application (e.g., a SMS text messaging application, the native wellness platform application) executing on the user's mobile computing device. For example, Block S160 can push the directive to the user in the form of a notification, and the user can access content of the directive by engaging a in a conversation within the native wellness platform application. In another example, Block S160 delivers the directive to the user before the user initiates an action defined in the behavioral pattern, such as when the method detects the user is substantially inactive before an expected walk. In yet another example, Block S160 delivers the directive to the user after the user completes an expected action, such as just after the user completes a walk and enters the native wellness platform application. In a further example, Block S160 delivers the directive to the user through the native wellness platform application after the user completes the expected action, the method predicts that the user is inactive, and the user opens the native wellness platform application.

However, Block 160 can deliver the directive to the user in any other form or format on any other suitable device and according to any other suitable trigger.

9. Variation: Density Clustering

In one variation, the method (e.g., Block S110) implements a data-clustering algorithm (e.g., a density-based spatial clustering of applications with noise (DBSCAN) algorithm) to detect a behavioral pattern of the user.

In this variation, Block S102 collects user activity events recorded over a period of time, such as fourteen days or ten weeks, and then groups these recorded user activity events by activity type, such as by running, walking, eating, driving, and/or working, etc. to form a record of activity events of a particular activity type, as described above. Block S110 subsequently filters these grouped user activity events into activity buckets (or sub-groups) according to conditions of the grouped user activity events. In one example, Block S110 filters grouped activity events by time, such as by day of the week (e.g., every Monday), by every other weekday (e.g., every other Tuesday), by weekdays (i.e., Mondays through Fridays), by weekends (i.e., Saturdays and Sundays), etc. on which each recorded activity in a group of activities occur, such as described above. Thus in this example, Block S110 can apply a filter to a group of walking events for the user to aggregate buckets of walking events performed by the user every weekday, every other Wednesday, and/or every Sunday. Block S110 can also apply a filter to a group of driving events to filter the group (record) of driving event into buckets of driving events performed by the user on weekdays, weekends, and every other Friday, etc.

Block S110 can also filter groups of activity events (of a particular type) according to other dimensions of data collected and stored with in records of the activity events in the group, as described above. For example, Block S110 can filter groups of activity events by user location, such as proximity to common locations within static or dynamic distance ranges (e.g., within Soft of the user's home, within 100 ft of the user's office, and within 500 ft of a school of the user's child, etc.). Block S110 can additionally or alternatively filter groups of user activity events by corresponding local weather condition, such as average daily temperature, local rain or snowfall within a coincident period of time, by minimum and/or maximum visibility (e.g., from fog, from smog), and/or by cloud cover. Block S110 can thus filter a relatively large record of activity events completed over a period of time (e.g., fourteen days or ten weeks) into buckets of activity events completed under similar day, location, weather, and/or other condition.

Figure 3:
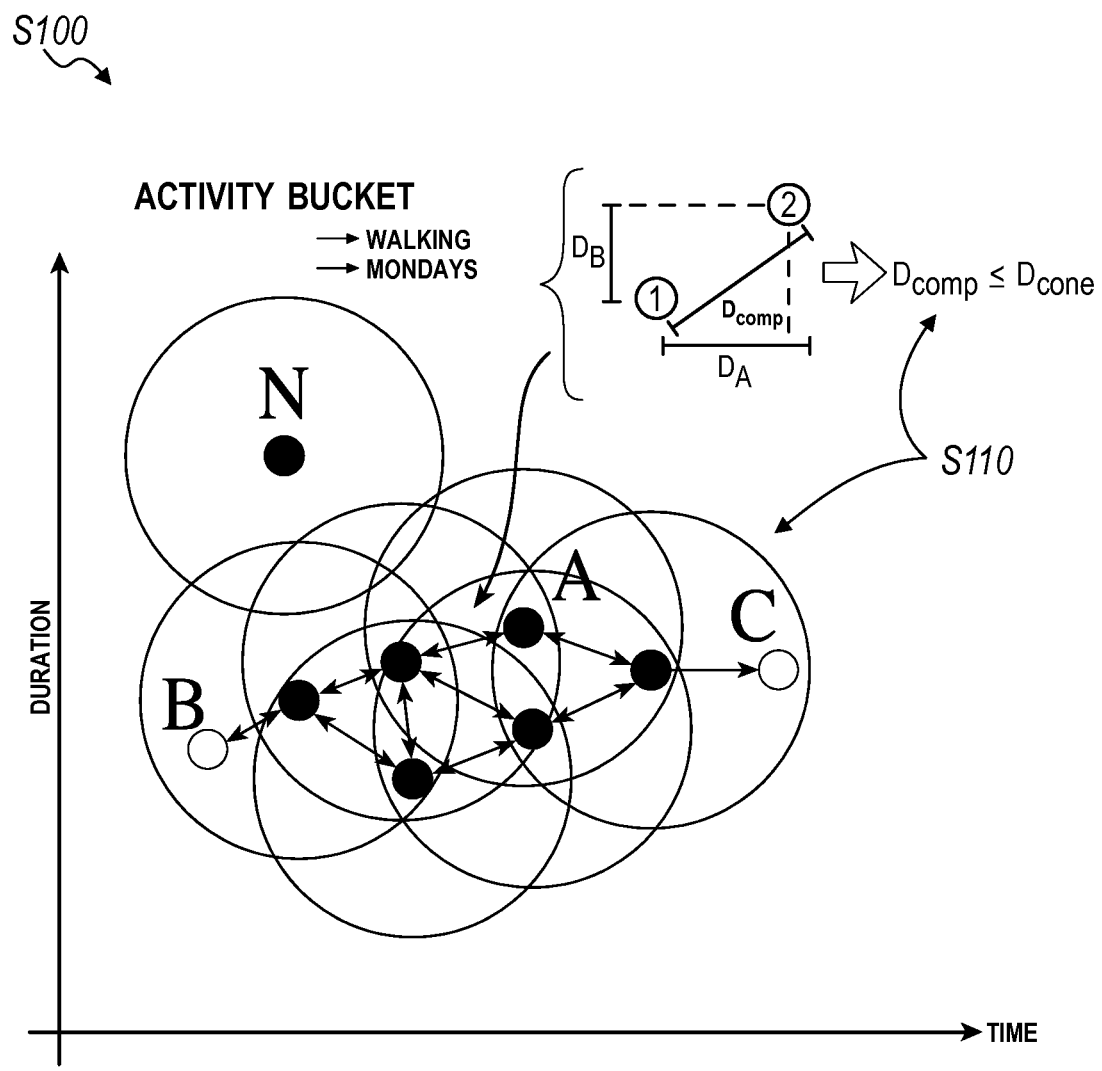
FIG. 3 is a flowchart representation of one variation of the method.

In this variation, Block S110 then passes buckets of activity events (e.g., walking events on Mondays) into a data-clustering algorithm to detect a behavioral pattern of the user. In one implementation, Block S110 (graphically or mathematically) plots each activity event in an activity bucket as a point on a graph with time of day of initiation of an activity event represented on a first (e.g., X-) axis of the graph and a duration of an event on a represented on a second (e.g., Y-) axis of the graph, as shown in FIG. 3. In this variation, Block S110 can thus calculate and analyze (virtual, graphical) distances between points—corresponding to activity events in the bucket—on the graph to identify clusters of related activity events indicating one or more behavioral patterns.

In one implementation, Block S120 can plot on the graph a group of points that fall within a core threshold distance from at least one other point within the group, and the group of points can thus define "core" points on the graph, such as group "A" shown in FIG. 3. In this implementation, Block S120 can also plot a second point that falls at a distance from a nearest core point that exceeds the core threshold distance but is less than a density-reachable threshold, and this second point can thus define a "density-reachable" point on the graph, such as the point at "B" and the point at "C" shown in FIG. 3. Furthermore, in this implementation, Block S120 can plot a third point that falls at a distance from a nearest core point or from a density-reachable point exceeding the density-reachable threshold, and this third point can thus define a "noise" point on the graph, such as the point at "N" shown in FIG. 3. Thus, in this implementation, Block S110 can determine presence of a behavioral pattern (e.g., a habit) from the graph if a cluster of core points shown on the graph includes at least a threshold number of core points, such as three core points. Additionally or alternatively, in this implementation, Block S110 can identity a behavioral pattern if a cluster of core and density-reachable points includes at least a threshold number of points, such as four total core or density-reachable points.

As in the foregoing implementation, Block S110 can apply a distance algorithm to points on the graph based on conditions of the corresponding activity events to identify activity clusters indicative of user behavioral patterns. In one implementation, when plotting a first activity event from an activity bucket onto the graph, Block S110 can convert a time of initiation of the first activity event into a time (e.g., minutes or seconds) from a common time anchor (e.g., midnight) and label this time as $T_1$. Block S110 can also convert a time of initiation of a second activity event into a time from the common time anchor and label this time as $T_2$. (Block S110 can also scale $T_1$ and $T_2$, such as by a factor of 200 or 0.005.) Block S110 can subsequently determine a "time distance" between the first and second activity events by calculating a difference between $T_1$ and $T_2$ and label this $D_A$. (Block S110 can also scale $D_A$, such as by a factor of 100 or 0.01.) For example, Block S110 can calculate a time distance between two walking events beginning at 12:19:31 PM (±0:00:27) on two consecutive Mondays as ~0.0 time distance units, as these walking events are substantially identical for the time of day condition. In this example, Block S110 can calculate a time distance between a first walking event beginning at 12:19 PM on a first Monday and a second walking event beginning at 12:23 PM on a second Monday as 2.873 time distance units, and Block S110 can calculate a time distance between the first walking event and a third walking event beginning at 12:01 PM on a third Monday as 14.588 time distance units. Block S110 can thus calculate time distances between (substantially) all points in the activity bucket.

In the foregoing implementation, Block S110 can also determine a "duration distance" between the first and second activity events in the bucket by calculating a proportional difference between the duration of the first activity event and the duration of the second activity event and can then pass this proportional difference through an exponential function. Block S110 then labels the output of the exponential function $D_B$. For example, Block S110 can calculate a duration distance between two walking events of duration 0:16:31 (±0:00:11) as ~0.0 duration distance units, as these event are of substantially similar duration. In this example, Block S110 can calculate a duration distance between a first walking event of duration 0:16:31 and a second walking event of duration 0:17:59 as 3.677 duration distance units, and Block S110 can calculate a duration distance between the first walking event and a third walking event of duration 0:14:03 as 53.810 duration distance units. Block S110 can thus calculate duration distances between (substantially) all points in the activity bucket.

In this implementation, Block S110 can plot points corresponding to activity events in the activity bucket onto the graph that represents additional dimensions of activity events, such as locations coincident an activity event, an intensity of an activity event, distance traversed during an activity event, quality an activity event, etc. In particular, Block S110 can (virtually, mathematically) manipulate a graph including additional (e.g., a third, a fourth, a fifth) axes label according to additional dimensions of the activity events within the bucket. For example, for a bucket that further includes locations coincident activity events contained therein, Block S110 can plot the activity events on a graph further including a third (e.g., Z-) axis representing location (e.g., distance from an anchor point); similarly, Block S110 can plot the activity events on a graph further including a third (e.g., Z-) axis representation longitudinal location (e.g., longitudinal distance from an anchor point) and including a fourth (e.g., R-) axis representation latitudinal location (e.g., latitudinal distance from an anchor point). Block S110 can thus implement methods or techniques as described above to determine a mathematical "location distance" between the first and second activity events based on a physical distance between a geospatial location (e.g., GPS coordinates) associated with the first activity event and a geospatial location associated with the second activity event. In one example, when plotting the first activity event in the activity bucket onto the graph, Block S110 converts a location of initiation of the first activity event into a distance (e.g., feet, miles) from a common location anchor (e.g., the user's home) and labels this distance as $d_1$. Block S110 also converts a time of initiation of the second activity event into a distance from the common location anchor and labels this distance as $d_2$. (Block S110 can also scale $d_1$ and $d_2$ as described above.) Block S110 subsequently determines a "location distance" between the first and second activity events by calculating a difference between $d_1$ and $d_2$ and labels this $D_C$.

In the foregoing example, Block S102 can thus retrieve, from a database, a record of activity events further specifying a location coincident performance of each activity event, in the record of activity events, by the user, and Block S110 can select a subgroup of activity events corresponding to locations within a threshold distance of a location corresponding to at least one other activity event within the subgroup of activity events to identify a cluster of activity events indicative of a behavioral pattern. From the cluster of activity events, Block S110 can identify a particular geographic location associated with the activity events of the particular activity type represented by the cluster. Block S140 can then set a threshold distance from the particular geographic location for activity events of the particular activity type for the user; and Block S160 can communicate a notification (e.g., a notification of the first type) to the user via the user's mobile computing device based on presence of the computing device within the threshold distance of the particular geographic location when other conditions of the cluster are met, such as an early bound on the activity event is detected or approaching on a day fulfilling time-based filter applied to the record of activity events in Block S110.

In another example, Block S102 retrieves a record of activity events further specifying a second activity event distinct from the first activity type and preceding each activity event in the record of activity events by a known lead time, and Block S110 implements the foregoing methods can techniques to identify a subgroup of activity events, in the record of activity events, preceded by second activities of a second activity type and corresponding to lead times less than a maximum lead time specified in a selected time-based filter, such as by plotting occurrence, lead time, intensity, and/or duration of instances of events of the second activity type on a third (e.g., Z) axis of the (virtual) graph. In this example, Block S160 can thus communicate a notification of the first type to the user in response to detecting an activity of the second type prior to the early bound on a day fulfilling the first time-based filter.

Block S110 can also plot points corresponding to activity events in the activity bucket on the (imaginary) graph that additionally or alternatively includes weather condition on a fourth (e.g., A-) axis. Block S110 can thus implement similar methods or techniques to determine a mathematical "weather distance" between the first and second activity events based on a physical distance (e.g., in feet or miles) between a geospatial location (e.g., GPS coordinates) associated with the first activity event and a geospatial location associated with the second activity event. In one example, when plotting the first activity event in the activity bucket onto the graph, Block S110 converts an average local ambient temperature (or other weather condition) during the first activity event into a quantitative metric and labels this metric as $W_1$. Block S110 also converts an average local ambient temperature during the second activity event into a quantitative metric and labels this metric as $W_2$. Block S110 subsequently determines a "weather distance" between the first and second activity events by calculating a difference between $W_1$ and $W_2$ and labels this $D_D$. However, Block S110 can calculate a weather distance between two "plotted" points according to any other one or combination of weather conditions (e.g., temperature, barometric pressure, rainfall, snowfall, fog, etc.).

Block S110 can subsequently combine the time distance (e.g., $D_A$), the duration distance (e.g., $D_B$), the location distance (e.g., $D_C$), and/or the weather distance (e.g., $D_D$) into a composite distance (e.g., $D_{comp}$) for each point in the group of points corresponding to the bucket of activity events. For example, Block S110 can implement a form of the Pythagorean theorem, such as $D_{comp}^2 = D_A^2 + D_B^2 + D_C^2 + D_D^2$ or $D_{comp}^2 = aD_A^2 + bD_B^2 + cD_C^2 + dD_D^2$ (wherein a, b, c, and d are weight coefficients), to calculate a minimum distance between the group of points plotted on a two-dimensional (e.g., time and duration), three-dimensional (e.g., time, duration, and location), four-dimensional (e.g., time, duration, location, and weather), or other-dimensional (mathematical or virtual) graph. Block S110 can thus identify each point in the group as a core, density-reachable, or noise point based on such composite distances from all or nearest points on the graph, as described above. Once points in the group—and therefore corresponding activity events in the bucket—are characterized, Block S110 can tabulate a number of core and/or density-reachable points on the graph and estimate a behavioral pattern (i.e., a habit) if the total number of core and/or density-reachable points exceeds a pattern threshold, as described above.

Block S110 can also identify multiple clusters of core and/or density-reachable points on the graph, such as if a number of core and density-reachable points on the graph exceeds threshold number, and Block S110 can thus identify multiple behavioral patterns (e.g., habits) from one bucket of activity events. For example, Block S110 can calculate a centroid of all core and density-reachable points in the group, calculate a maximum and a minimum distance between the centroid and the core and density-reachable points in the group, and then search for a second behavioral pattern if the difference between the maximum and the minimum distances between the centroid and the core and density-reachable points exceeds a threshold.

Block S110 can further update the graph with new plotted activity events as new activity events are recorded (e.g., at 12:01 AM every night) and then recalculate distances between plotted points on the graph, re-characterize the points on the graph, and re-calculate a behavioral pattern(s) from characterizations of the plotted points. For example, as additional user activity data is collected over time, Block S110 can analyze a trajectory of a cluster of points relative to old point clusters to confirm predicted strengthening and/or weakening of the detected behavioral pattern(s). In another example, as new activity events are added to the graph as points based on new user data collected over time, Block S110 can determine that activity events that were previously classified as a single behavioral pattern are, in fact, two distinct behavioral patterns (or habits) as one cluster of points splits into two distinct clusters over time, such as shown in FIG. 4. In this example, Block S110 can automatically adjust coefficients of the exponential function, scaling values, and/or weight coefficients in the distance equation described above, etc. to enable earlier detection of division of points into two clusters in similar instances for other user data. Specifically, Block S110 can re-process previous activity events in an activity bucket and adjust coefficients, thresholds, and/or weights, etc. to minimize divisions and mergers among activity clusters within the activity bucket. Block S110 can thus implement machine learning techniques to improve the data-clustering algorithm (i.e., coefficients of the data-clustering algorithm) substantially without input from the user, a coach, or an other human entity or user.

For example, Block S102 can collect addition user data in the form of a second record of activity events of the particular activity type performed by the user over a second period of time succeeding the (first) period of time, wherein the second record similarly specifies a start time and a duration of each activity event in the second record of activity events. In this example, Block S110 can then select a second time-based filter from a set of time-based filters to apply to a combination of the (first) record and the second record of activity events and thus identify a second cluster of activity events in a combination of the first and second records filtered according to the second time-based filter. Block S140 can thus identify an alternative early bound and an alternative late bound on start times of activity events of the particular activity type from the second cluster of activity events, and Block S160 can communicate a notification of the first type to the user at a third time succeeding the second period of time and within a threshold time of the alternative early bound on a day fulfilling the second time-based filter. Block S150 can also communicate a notification of the second type to the user at a fourth time succeeding the second period of time and within a threshold time of the alternative late bound on a day fulfilling the second time-based filter.

Block S110 can further adjust the time anchor based on density and/or type of user activity performed during periods of a day (or other time period). For example, if a user is commonly active at night until around 2 AM and often sleeps between 2:30 AM and 11 AM, Block S110 can shift the time anchor from 12 AM to 5 AM. In this example, Block S110 can also set the end-of-day (or new day) time to 5 AM, and Block S110 can thus group, filter, and process the past day's user activity events with previous activity events in corresponding buckets at or soon after 5 AM each day. In particular, in this example, Block S110 can redefine a time definition of a "day"—that is, when a day starts and ends for purposes of analyzing the user's activity events—thereby accommodating the user's habits or behavioral patterns that occur at or around key times (e.g., at or around midnight).

Block S110 can further compare discrete identified behavioral patterns for different activity types (e.g., walking and working) by one or more corresponding conditions (e.g., time of day, day of week, weekday, duration, location, average temperature, and/or rainfall, etc.) to extrapolate co-occurrence of two or more habits. For example, Block S110 can determine that the user has regular meetings at 4 PM on Tuesdays and occasionally has meetings at 4 PM on Wednesday and does not exercise in the evenings on Tuesdays and most Wednesdays on which the user has a 4 PM meeting schedules.

Furthermore, in this variation, Block S120 can classify a strength of the user's behavioral pattern based on a cluster density of core and/or density-reachable points plotted (graphically or mathematically in the algorithm) in Block S110. For example, Block S120 can average a composite (e.g., time and duration) distance between all core points in a cluster and calculate a strength of a behavioral pattern that is inversely proportional to the average composite distance between the core points in the corresponding cluster. In particular, as in this example, as a cluster of core or density-reachable points—corresponding to a bucket of activity events—increases in density (e.g., decreases in area or volume), Block S120 can determine that the user is strengthening the corresponding activity as a behavioral pattern.

In this variation, Block S130 can track changes in the time distance for a particular activity bucket as new user activity data is collected over time and correlate decreasing time distances with increasing user consistency in performing a particular activity, thereby strengthening the behavioral pattern, and vice versa. Block S130 can additionally or alternatively track changes in the duration distance for the particular activity bucket and correlate increased duration with positive user intent to build a habit and/or increase health and wellness (for a positive behavior). Block S120 can thus analyze conditions and/or condition distances of points corresponding to an activity bucket to identify and track commitment and responsiveness to a behavior or habit.

9.1 Static Start Time Ranges

In a similar variation, Block S110 sets a length of a start time test window (e.g., sixty minutes) and tests the start time test window to the (virtual, mathematical) graph of points representing activity events identify subgroups of points indicative of a behavioral pattern, as shown in FIG. 6. In particular, Block S110 can filter the record of activity events by a selected time-based filter (e.g., activity events occurring on Mondays and Wednesdays) and then apply a start time test window to start times of the filtered set of activity events to identify clusters of related activity performed by the user over time.

In one implementation, Block S110 aggregates start times of activity events in the bucket into a daily timeline and then pass the start time test window over the timeline to identify a peak number of start times coincident the start time test window; Block S110 can thus identify a user behavioral pattern from the corresponding activity events. Similarly, Block S110 can pass the start time test window over the timeline to identify discrete instances of the test window applied along the timeline containing at least a minimum (threshold) number of start times, and Block S110 can thus correlate a user behavioral pattern with each discrete instance of the test window fulfilling the filter and minimum number of start times. Block S110 can thus identify a subgroup of activity events—in the record of activity events—corresponding to start times falling within a threshold time from a start time of at least one other activity event within the subgroup of activity events. Block S130 can then characterize an identified subgroup of activity events as one of a pre-habit behavior and a habit based on the number of activity events in the subgroup of activity events, such as described above.

Figure 7:
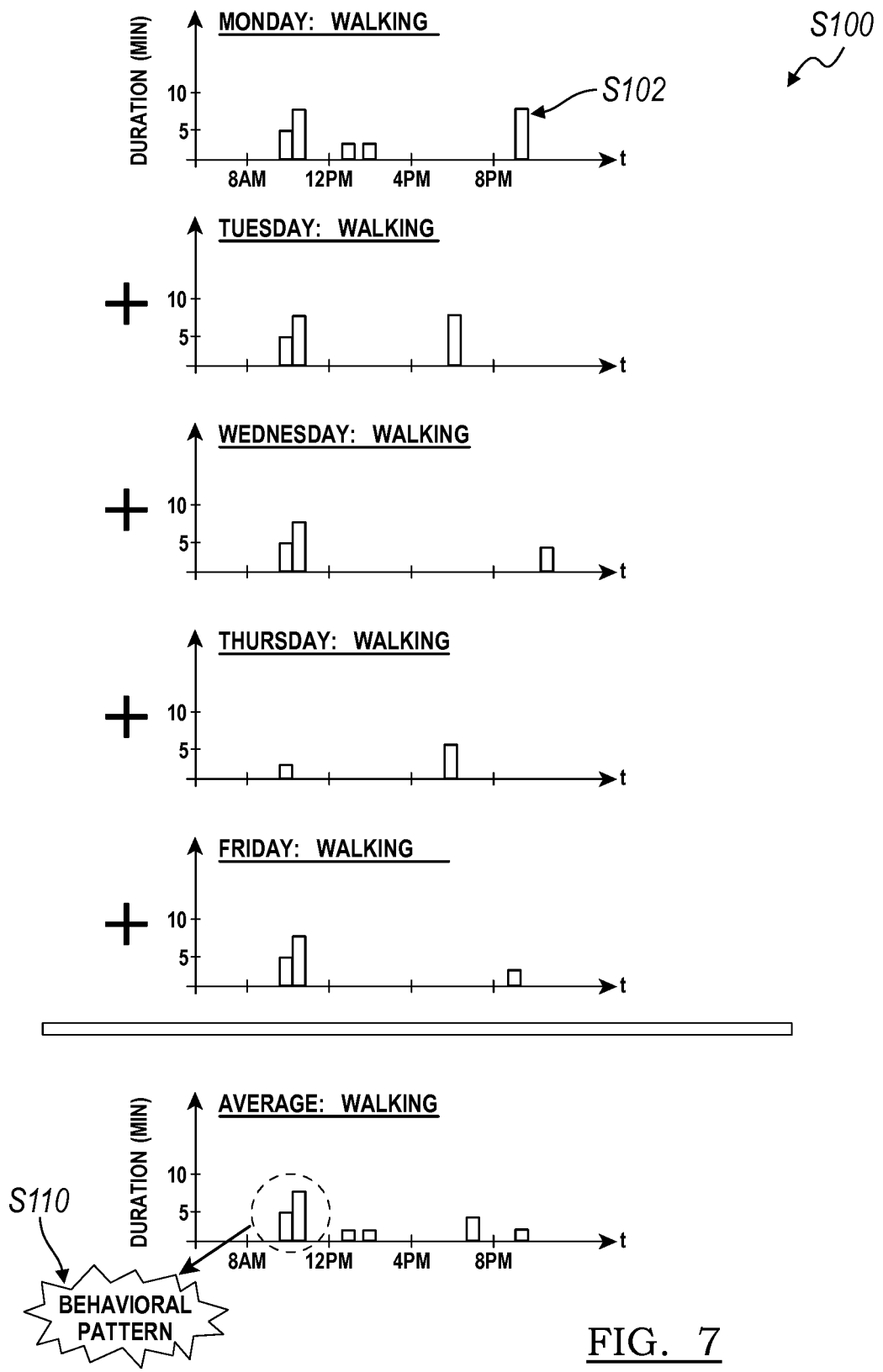
FIG. 7 is a flowchart representation of one variation of the method.

In a similar implementation, Block S110 identifies a set of days (or other periods of time) (e.g., all weekdays) within the record of activity events fulfilling elected time-based filters for the behavioral pattern and then aggregates a (virtual) timeline of start times of discrete activities events— of the particular activity type—performed by the user for each day in the set of days. In this implementation, Block S110 then averaged the duration of each discrete activity event across the set of days for a series of discrete time windows per day to generate an averaged (virtual) timeline of durations of discrete activities events—of the particular activity type—performed by the user throughout the record of activity events, as shown in FIG. 7. Block S110 then identifies one or more clusters of average activity events within the averaged timeline and analyzes data within the record to determine a number of days in the set of days on which the user performs an activity event of duration at least a threshold proportion (e.g., 80%) of the average duration corresponding to each identified cluster in the averaged timeline. Block S110 can thus determine that a cluster in the averaged timeline corresponds to a behavioral pattern if the number of days on which the user performs an activity event of duration at least a threshold proportion of the average duration exceeds a threshold number of days (e.g., six days) or a threshold proportion of days within the set of days selected for the record (e.g., at least seven days in a set of ten days, or at least seven days in a two-week period of weekdays). Block S110 can also prioritize or rank behavioral patterns based on the number of days on which the user performs an activity event of duration at least a threshold proportion of the average duration for each identified cluster in the averaged timeline.

In one example, Block S110 can implement the foregoing methods and techniques to identify a walking-related behavioral pattern based on start times and durations of walking events performed by the user over a set of days (e.g., weekdays). Block S110 can similarly implement the foregoing methods and techniques to identify a sleeping-related behavioral pattern based on start times and durations of sleeping periods performed by the user over a set of days, to identify an exercise (e.g., running, swimming)-related behavioral pattern based on start times and durations of exercise events performed by the user over a set of days, to identify a working-related behavioral pattern based on start times and durations of working periods performed by the user over a set of days, etc. Block S110 can additionally or alternatively implement the foregoing methods and techniques to identify user behavioral patterns based on start times of activity events and one or more other dimensions of the activity events, such as location, intensity, distance traversed, quality, etc.

In the foregoing implementation, Block S110 can also weight days in the set of days when averaging durations of discrete activity events across the set of days to generate the averaged (virtual) timeline, such as by weighting activity event data of more recent days greater than activity event data of days further in the past.

9.1 Bounds

In this variation, Block S140 can set trigger points at condition boundaries for a cluster of core and/or density-reachable points plotted in Block S110 and arm a recommendation for delivery to the user if condition of a newly-entered activity event falls outside of one or more condition boundaries. In particular, Block S140 can identify an early bound on start times of activity events of the particular activity type from the cluster of activity events and identify a late bound on start times of activity events of the particular activity type from the cluster of activity events. For example, as shown in FIGS. 5A and 5B, Block S140 can set an early bound (e.g., a low time of day boundary) and a late bound (e.g., a high time of day boundary) for a time of day condition for a particular activity type in an activity bucket and trigger delivery of a related notification to the user if the start time of a new and related activity event occurs outside of the low and high time of day boundaries. In particular, in this example, Block S140 can set an early bound to trigger delivery of a habit consistency-related notification (i.e., a notification of a first type) to the user in response to approach of the early bound on start time of the activity event on a day in which the user is predicted to perform the activity type according to the behavioral pattern (i.e., on a day fulfilling one or more time-based filters selected and implemented by Block S110). Similarly, in this example, Block S140 can set a late bound to trigger delivery of a prompt for behavior deviation feedback (i.e., a notification of a second type) to the user in response to passage of the late bound and absence of a detected activity of the activity type on a day in which the user is predicted to perform the activity type according to the behavioral pattern.

Thus, in this example, Block S160 can deliver a notification to the user if a new point—corresponding to a new activity event in the bucket—added to the graph falls outside of a range bounded by a first line representing the low bound and a second (parallel and offset) line representing the high bound on a two-dimensional graph, as shown in FIG. 5B. Similarly, Block S160 can deliver a notification to the user if a new point added to the graph falls outside of a range bounded by a first plane representing the low bound and a second (parallel and offset) plane representing the high bound on a three-dimensional graph, as shown in FIG. 5A.

In another example, Block S140 can set a low duration boundary and a high duration boundary for a duration condition for a particular activity type in an activity bucket and trigger delivery of a related notification to the user if the duration of a new and related activity event falls outside of the low and high duration boundaries. Blocks S140 and S160 can thus cooperate to delivery intent- or magnitude-related notifications for activity events performed—or not performed—by the user.

9.1 Notifications

In the foregoing variation, Block S160 can, at a first time succeeding the period of time, communicate a notification of a first type to the user, wherein the first time falls within a threshold time of the early bound—set in Block S140—on a day fulfilling the first time-based filter applied to the record of activity events in Block S110 to identify the behavioral pattern. Generally, in this variation, Block S160 can present a notification (e.g., a directive, a reminder, a relevant user statistic, etc.) of the first type to the user preemptively and before the user is predicted to begin an activity of the associated activity type.

In one implementation, Block S160 generates or selects a reminder (of a first type) to perform the activity event and presents the reminder to the user at some time before (e.g., one minutes before) the early bound on a start time of an activity event corresponding to the behavioral pattern. For example, for an early bound of 7:30 AM on weekdays for a behavioral pattern characterized by 22±3 minutes of walking, Block S160 can deliver to the user—at 7:29 AM on a Wednesday (or other weekday)—a reminder to walk for about 20 minutes. In another implementation, Block S160 generates or selects a prompt (of a first type) to change (e.g., increase, improve) a second dimension of an activity event that the user is predicted to begin soon, as determined by the behavioral pattern, and delivers the prompt to the user prior to anticipated initiation of the activity event by the user. For example, for an early bound of 7:30 AM on weekdays for a behavioral pattern characterized by 22±3 minutes of walking, Block S160 can deliver a prompt to walk for longer than 22 minutes—such as, "Walk a little longer than usual today by taking this alternate route to your office" accompanied by a map of the alternate route—to the user at 7:29 AM on a Wednesday (or other weekday) just before the user is predicted to begin a common (e.g., habitual) walking event. In this implementation, Block S160 can similarly prompt the user to run faster, walk further in less time, sleep better, burn more calories, or other modify a second (or other) dimension of an activity event prior to initiation of the activity event by the user.

In another implementation, Block s160 extrapolates—from a detected cluster of activity events—a quantitative datum corresponding to the particular activity type and presents a form of the quantitative datum to the user (e.g., through his mobile computing device) inside a notification of the first type. In one example, Block S110 calculates a probability of initiation of an activity of the particular activity type, by the user, between the early bound and the late bound on a current date and predicts a duration of the activity based on the cluster of activity events; and Block S160 then renders the probability of initiation of the activity and the duration of the activity within in a notification on a display of the user's mobile computing device in response to instance of a time within a threshold time of (e.g., two minutes prior to) the early bound on a day fulfilling the first time-based filter. In particular, in this example, Blocks S110 and S160 can cooperate assemble a prompt reciting, "At least 62% of days like today, you walk at least 80% of the target duration of 20 minutes and begin your walk around 7:30 AM, give or take 22 minutes;" Block S160 ca thus deliver the statistic in a notification of the first type to the user prior to anticipated initiation of the walking event by the user.

In the foregoing variation, Block S160 can further function to communicate a notification of a second type to the user at a second time succeeding the period of time, the second time within a threshold time of the late bound on a day fulfilling the first time-based filter. Generally, in this variation, Block S160 can present a notification (e.g., a directive, a reminder, a relevant user statistic, etc.) of the second type to the user following a period corresponding to predicted performed of an activity event by the user.

In one implementation, in response to absence of a detected activity of the particular activity type between the early bound and the late bound on a day fulfilling the first time-based filter, Block S160 presents to the user (e.g., through the user's mobile computing device) a prompt to provide feedback for the absence of a detected activity of the particular activity type, that is, feedback for why the user did not perform the anticipated activity event or otherwise deviated from the behavioral pattern. For example, Block S160 can deliver to the user a notification including a prompt to provide feedback to the native wellness platform application and a link or other pointer to a form or other interface for providing such feedback. For example, Block S160 can initiate a conversation with the user, such as described in U.S. Provisional Application No. 61/916,701, to collect user feedback from within a text-based two-way messaging service executing within the native wellness platform application. Block S160 can then pass feedback thus collected from the user back to Block S110 to retrain the cluster and to identify an alternative or modified behavioral pattern.

In another implementation, Block S160 generates and delivers to the user a notification prompting the user to complete at least portion of the activity type, even though the user's typical start time for the activity event has passed.

Block S160 can also generate a notification of the first type or of the second type based on a characterization of the cluster (e.g., subgroup) of activity events as one of a pre-habit behavior and a habit, as described above.

9.2 Feedback

In one variation, the method reprocesses user activity data to identify new behavioral patterns and/or to identify changes in the user's behavioral patterns over time as new user data becomes available.

In one implementation, Block S160 collects feedback from the user responsive to absence of performance of an anticipated activity event by the user, and Block S110 implements this feedback to select an alternative time-based filter from the set of time-based filters and applies this alternative time-based filter to the record of activity events to identify an alternative cluster of activity events, as described above. For example, Block S160 can prompt the user—through the messaging service—to provide feedback for missing an anticipated walking event on the first Tuesday of a month, and the user can enter a response—into the messaging service—stating, "I don't have time today. We have board meetings on the first Tuesday of every month." In this example, Block S110 can thus select a filter specifying monthly time cycle for repetition of the behavior pattern and excluding the first Tuesday of each month from days on which the user performs the corresponding activity event and then repeat methods and techniques described above to better characterize the user's behavioral pattern based on real user feedback collected after user deviation from a previously-identify behavioral pattern. In particular, Block S110 can then identify a second cluster of activity events in the record of activity events filtered according to the alternative time-based filter; Block S140 can identify an alternative early bound on start times of activity events of the particular activity type from the second cluster of activity events and identify an alternative late bound on start times of activity events of the particular activity type from the alternative cluster of activity events; and Block S160 can communicate notifications to the user at later times based on the alternative early bound, the alternative late bound, and the alternative time-based filter, as described above.

Blocks of the method can implement similar methods and techniques to update the behavioral pattern if an anticipated activity event is not performed by the user within the early and late bounds defined by the behavioral pattern. However, Blocks of the method can automatically retrain the cluster of activity events to identify a new behavioral pattern or a change in a previously-identified behavioral pattern in response to receipt of any other user data over time.

The systems and methods of the foregoing embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for communicating activity-related notifications to a user, the method comprising:
    receiving, at a remote computer system from a wireless communication transceiver module of a mobile computing device, a record of activity events of a particular activity type performed by the user over a period of time, the record specifying a start time and a duration of each activity event in the record of activity events, wherein receiving the record of activity events comprises collecting location data sampled at a location sensor of the mobile computing device comprising the location sensor, a display, and the wireless communication transceiver module, wherein the location data comprises a location coincident performance of each activity event by the user;
    selecting, at the remote computer system, a first time-based filter from a set of time-based filters for the record;
    identifying, at the remote computer system, a cluster of activity events in the record of activity events filtered according to the first time-based filter, wherein identifying the cluster of activity events in the record of activity events comprises:
        obtaining a set of computer-implemented rules defining activity event subgrouping as a function of activity event start time, activity event duration, and coincident location, wherein the set of computer-implemented rules are operable to improve the remote computing system in relation to behavioral pattern prediction, and selecting a subgroup of activity events according to the set of computer-implemented rules and corresponding to:
  composite start times and durations falling within a core composite distance threshold of a composite start time and a duration of at least one other activity event within the subgroup of activity events, and
  locations, from the location data sampled at the location sensor, within a threshold distance of a location corresponding to at least one other activity event within the subgroup of activity events; and
predicting, at the remote computer system, representation of a behavioral pattern of the user in the subgroup based on identification of the cluster;
identifying, at the remote computer system, an early bound on start times of activity events of the particular activity type from the cluster of activity events;
identifying, at the remote computer system, a late bound on start times of activity events of the particular activity type from the cluster of activity events;
at a first time succeeding the period of time, communicating a notification of a first type to the user for presentation at the display of the mobile computing device, the first time within a threshold time of the early bound on a day fulfilling the first time-based filter; and
at a second time succeeding the period of time, communicating a notification of a second type to the user for presentation at the display of the mobile computing device, the second time within a threshold time of the late bound on a day fulfilling the first time-based filter.

2. The method of claim 1, wherein receiving the record of activity events comprises collecting a first set of action data of the user from a wearable device worn by the user during the period of time, collecting a second set of action data of the user from a mobile computing device associated with the user during the period of time, fusing the first set of action data and the second set of action data into discrete activity events performed by the user during the period of time, and filtering the discrete activity events by the particular activity type to assemble the record of activity events.

3. The method of claim 1, wherein receiving the record of activity events comprises retrieving, from a database, a record of walking events performed by the user over a sequence of days, the record specifying a start time and a duration of each walking event in the record of walking events; wherein selecting the first time-based filter from the set of time-based filters comprises selecting the first time-based filter specifying a minimum duration of a walking event and a particular subset of weekdays; and wherein identifying the cluster of activity events in the record of activity events comprises discarding walking events, in the record of walking events, of duration less than the minimum duration and occurring on days outside the particular subset of weekdays.

4. The method of claim 3, wherein selecting the first time-based filter comprises selecting the first time-based filter from the set of time-based filters comprising a filter specifying a single weekday, a filter specifying a combination of two weekdays, a filter specifying a combination of three weekdays, a filter specifying a combination of four weekdays, a filter specifying a combination of five weekdays, a filter specifying a single weekend day, and a filter specifying a combination of weekend days.

5. The method of claim 1, wherein identifying the cluster of activity events in the record of activity events comprises:
  identifying activity events in the subgroup as core points;
  selecting a second subgroup of activity events, in the record of activity events, corresponding to composite start times and durations exceeding the core composite distance threshold and falling within a density-reachable threshold distance of a composite start time and duration of an activity event within the subgroup of activity events;
  identifying activity events in the second subgroup as density-reachable points;
  calculating a centroid of core points and density-reachable points in the subgroup and the second subgroup;
  calculating a maximum distance and a minimums distance between the centroid and the core points and between the centroid and the density-reachable points; and
  predicting representation of a minimum of two behavioral patterns in the subgroup and the second subgroup in response to a difference between the maximum distance and the minimum distance exceeding a threshold.

6. The method of claim 1,
  further comprising, from the cluster of activity events, identifying a particular geographic location associated with the activity events of the particular activity type;
  further comprising setting a threshold distance from the particular geographic location for activity events of the particular activity type for the user;
  wherein communicating the notification of the first type to the user comprises communicating the notification of the first type through a mobile computing device associated with the user based on presence of the computing device within the threshold distance of the particular geographic location on a day fulfilling the first time-based filter.

7. The method of claim 1, wherein identifying the cluster of activity events in the record of activity events comprises identifying a subgroup of activity events, in the record of activity events, corresponding to start times falling within a threshold time from a start time of at least one other activity event within the subgroup of activity events.

8. The method of claim 1, further comprising identifying a user behavioral pattern for the particular activity type based on the subgroup of activity events comprising a number of activity events exceeding a threshold number of events.

9. The method of claim 8, wherein identifying the user behavioral pattern of the particular activity type comprises characterizing the subgroup of activity events as one of a pre-habit behavior and a habit based on the number of activity events in the subgroup of activity events; and wherein communicating the notification of the first type to the user comprises generating the notification of the first type based on a characterization of the subgroup of activity events as one of a pre-habit behavior and a habit.

10. The method of claim 1, wherein communicating the notification of the first type to the user comprises extrapolating, from the cluster, a quantitative datum corresponding to the particular activity type and presenting a form of the quantitative datum through a mobile computing device associated with the user.

11. The method of claim 10, wherein extrapolating the quantitative datum from the cluster comprises calculating a probability of initiation of an activity of the particular activity type, by the user, between the early bound and the late bound on a current date and predicting a duration of the activity of the particular activity type based on the cluster of activity events; and wherein presenting the form of the quantitative datum comprises rendering the probability of initiation of the activity and the duration of the activity within in a notification on a display of the mobile computing device in response to instance of a time within a threshold time of the early bound on a day fulfilling the first time-based filter.

12. The method of claim 10, wherein communicating the notification of the second type to the user comprises, in response to an absence of a detected activity of the particular activity type between the early bound and the late bound on a day fulfilling the first time-based filter, presenting to the user, through the mobile computing device, a prompt to provide feedback for the absence of a detected activity of the particular activity type.

13. The method of claim 12, further comprising:
receiving feedback for the absence from the user through the mobile computing device;
selecting an alternative time-based filter from the set of time-based filters based on the feedback;
identifying a second cluster of activity events in the record of activity events filtered according to the alternative time-based filter;
identifying an alternative early bound on start times of activity events of the particular activity type from the second cluster of activity events;
identifying an alternative late bound on start times of activity events of the particular activity type from the alternative cluster of activity events;
at a third time succeeding the period of time, communicating a notification of the first type to the user, the third time within a threshold time of the alternative early bound on a day fulfilling the alternative time-based filter; and
at a fourth time succeeding the period of time, communicating a notification of the second type to the user, the fourth time within a threshold time of the alternative late bound on a day fulfilling the alternative time-based filter.

14. The method of claim 1, further comprising:
receiving a second record of activity events of the particular activity type performed by the user over a second period of time succeeding the period of time, the second record specifying a start time and a duration of each activity event in the second record of activity events;
selecting a second time-based filter from a set of time-based filters for the record and the second record;
identifying a second cluster of activity events in a combination of the record of activity events and the second record of activity events filtered according to the second time-based filter, the second cluster comprising at least one activity event of the cluster;
identifying an alternative early bound on start times of activity events of the particular activity type from the second cluster of activity events;
identifying an alternative late bound on start times of activity events of the particular activity type from the second cluster of activity events;
at a third time succeeding the second period of time, communicating a notification of the first type to the user, the third time within a threshold time of the alternative early bound on a day fulfilling the second time-based filter; and
at a fourth time succeeding the second period of time, communicating a notification of the second type to the user, the fourth time within a threshold time of the alternative late bound on a day fulfilling the second time-based filter.

15. The method of claim 1:
wherein receiving the record of activity events comprises receiving the record further specifying a second activity event preceding each activity event in the record of activity events by a corresponding lead time;
wherein identifying the cluster of activity events in the record of activity events comprises identifying a subgroup of activity events, in the record, preceded by second activities of a second activity type corresponding to lead times less than a maximum lead time specified in the first time-based filter, the second activity type distinct from the first activity type; and
wherein communicating the notification of the first type to the user comprises communicating the notification of the first type to the user in response to detecting an activity of the second type prior to the early bound on a day fulfilling the first time-based filter.

16. The method of claim 1,
wherein receiving the record of activity events comprises collecting motion data sampled at an inertial sensor of the mobile computing device, wherein the motion data describes user motion coincident the performance of each activity event by the user, wherein the location data and the motion data are operable to improve the remote computer system in relation to activity type prediction, and the method further comprising:
classifying, at the remote computer system, the particular activity type performed by the user based on the location data and the motion data, wherein predicting representation of the behavioral pattern comprises predicting representation of the behavioral pattern based on classification of the particular activity type and the identification of the cluster.

17. A method for communicating activity-related notifications to a user, the method comprising:
receiving, at a remote computer system from a wireless communication transceiver module of a mobile computing device, a record of activity events of a particular activity type performed by the user over a period of time, the record specifying a time of each activity event in the record of activity events, wherein receiving the record of activity events comprises collecting location data sampled at a location sensor of the mobile computing device comprising the location sensor, a display, and the wireless communication transceiver module, wherein the location data comprises a location coincident performance of each activity event by the user;
selecting, at the remote computer system, a first time-based filter from a set of time-based filters for the record;
identifying, at the remote computer system, a cluster of activity events in the record of activity events filtered according to the first time-based filter, wherein identifying the cluster of activity events in the record of activity events comprises:
obtaining a set of computer-implemented rules defining activity event subgrouping as a function of activity event start time, activity event duration, and coincident location, wherein the set of computer-implemented rules are operable to improve the remote computing system in relation to behavioral pattern prediction, and
selecting a subgroup of activity events according to the set of computer-implemented rules and corresponding to:
composite start times and durations falling within a core composite distance threshold of a composite start time and a duration of at least one other activity event within the subgroup of activity events, and locations, from the location data sampled at the location sensor, within a threshold distance of a location corresponding to at least one other activity event within the subgroup of activity events; and predicting, at the remote computer system, representation of a behavioral pattern of the user in the subgroup based on identification of the cluster;

identifying, at the remote computer system, an early bound on times of activity events of the particular activity type from the cluster of activity events;

identifying, at the remote computer system, a late bound on times of activity events of the particular activity type from the cluster of activity events;

extrapolating, from the cluster, a quantitative datum corresponding to the particular activity type and the first time-based filter;

at a first time succeeding the period of time, presenting a form of the quantitative datum through the display of the mobile computing device associated with the user, the first time within a threshold time of the early bound on a day fulfilling the first time-based filter; and at a second time succeeding the period of time, in response to an absence of a detected activity of the particular activity type between the early bound and the late bound on a day fulfilling the first time-based filter, presenting to the user a prompt to provide feedback for the absence of a detected activity of the particular activity type, the second time within a threshold time of the late bound on a day fulfilling the first time-based filter.

18. The method of claim 17, further comprising:

receiving feedback for the absence from the user through the mobile computing device;

selecting an alternative time-based filter from the set of time-based filters based on the feedback;

identifying a second cluster of activity events in the record of activity events filtered according to the alternative time-based filter;

identifying an alternative early bound on times of activity events of the particular activity type from the second cluster of activity events; and identifying an alternative late bound on times of activity events of the particular activity type from the alternative cluster of activity events.

19. The method of claim 17, wherein identifying the cluster of activity events in the record of activity events comprises identifying a minimum number of activity events, in the record of activity events, corresponding to start times falling within a range of start times specified in the first time-based filter for a particular weekday.

20. The method of claim 17, wherein receiving the record of activity events of the particular activity type comprises receiving the record of activity events of the particular activity type comprising one of walking, exercising, eating, driving, working, and sleeping, the record further specifying a duration of each activity event in the record of activity events.

* * * * *